US012806244B2

(12) United States Patent
Weiss et al.

(10) Patent No.: US 12,806,244 B2
(45) Date of Patent: Nov. 24, 2026

(54) COMPOUNDS FOR USE IN THE TREATMENT OF PARKINSON'S DISEASE

(71) Applicant: UNIVERSITY OF THE WITWATERSRAND, JOHANNESBURG, Johannesburg (ZA)

(72) Inventors: Stefan Franz Thomas Weiss, Johannesburg (ZA); Eloise Van Der Merwe, Boksburg (ZA); Katelyn Cuttler, Cape Town (ZA); Monique Bignoux, Boksburg (ZA); Jessica Burns, Cape Town (ZA)

(73) Assignee: UNIVERSITY OF THE WITWATERSRAND, JOHANNESBURG, Johannesburg (ZA)

( * ) Notice: Subject to any disclaimer, the term of this patent is extended or adjusted under 35 U.S.C. 154(b) by 938 days.

(21) Appl. No.: 17/298,415

(22) PCT Filed: Nov. 28, 2019

(86) PCT No.: PCT/IB2019/060302

§ 371 (c)(1),
(2) Date: May 28, 2021

(87) PCT Pub. No.: WO2020/110067

PCT Pub. Date: Jun. 4, 2020

(65) Prior Publication Data

US 2022/0160824 A1 May 26, 2022

(30) Foreign Application Priority Data

Nov. 28, 2018 (ZA) ................................ 2018/08025

(51) Int. Cl.

| | |
|---|---|
| ***A61K 38/17*** | (2006.01) |
| ***A61K 31/137*** | (2006.01) |
| ***A61K 31/198*** | (2006.01) |
| ***A61K 45/06*** | (2006.01) |
| ***A61P 25/16*** | (2006.01) |

(52) U.S. Cl.

CPC .......... *A61K 38/177* (2013.01); *A61K 31/137* (2013.01); *A61K 31/198* (2013.01); *A61K 45/06* (2013.01); *A61P 25/16* (2018.01)

(58) Field of Classification Search

CPC .. A61K 38/177; A61K 31/137; A61K 31/198; A61K 45/06; A61P 25/16

See application file for complete search history.

(56) References Cited

U.S. PATENT DOCUMENTS 11,896,645 B2 * 2/2024 Weiss ....................... A61P 3/10
2009/0142408 A1 6/2009 Lin et al.
2018/0325997 A1 11/2018 Weiss et al.
2021/0277084 A1 * 9/2021 Weiss ....................... A61P 3/04
2023/0212250 A1 * 7/2023 Weiss .................. A61K 38/177 514/17.8

FOREIGN PATENT DOCUMENTS

EP 3 494 987 A1 6/2016
WO 2006/066247 A2 6/2006
WO 2013/042053 A2 3/2013
WO WO-2017077516 A2 * 5/2017 .......... A61K 38/177
WO 2020/008442 A2 1/2020

OTHER PUBLICATIONS

Tyrone et al. ("37 kDa LRP::FLAG enhances telomerase activity and reduces senescent markers in vitro," Oncotarget. Sep. 27, 2017;8(49):86646-86656) (Year: 2017).*
Nelson (et al. 2008. The 67 kDa laminin receptor: structure, function and role in disease. Biosci. Rep. 28:33-48) (Year: 2008).*
Jovanovic (et al. 2015. Novel patented therapeutic approaches targeting the 37/67 kDa laminin receptor for treatment of cancer and Alzheimer's disease. Expert Opinion on Therapeutic Patents 25[5]:567-582) (Year: 2015).*
Scheffold (et al. 2016. Telomere shortening leads to an acceleration of synucleinopathy and impaired microglia response in a genetic mouse model. Acta Neuropathologica Communications 4:87) (Year: 2016).*
Kim (et al. 2017. CRISPR-Cas9 Mediated Telomere Removal Leads to Mitochondrial Stress and Protein Aggregation. Int. J. Mol. Sci. 18:2093) (Year: 2017).*
Mayo Clinic (2018. Parkinson's disease-Diagnosis & Treatment. Captured by Wayback Machine on Apr. 2, 2018. Available online at mayoclinic.org/diseases-conditions/parkinsons-disease/diagnosis-treatment/drc-20376062) (Year: 2018).*
Mayo Clinic (Parkinson's Disease. Available online at mayoclinic.org. Accessed on May 17, 2024) (Year: 2024).*
ThermoFischer Scientific (Overview of Protein Expression Systems. Available online at thermofisher.com. Accessed on Jun. 26, 2025 (Year: 2025).*
Tsuboi (et al. 2005. Alpha-synuclein overexpression in oligodendrocytic cells results in impaired adhesion to fibronectin and cell death. Mol. Cell. Neurosci. 29:259-268)) (Year: 2005).*
Panegyres (and Armari. 2013. Therapies for human prion diseases. Am. J. Neurodegener. Dis. 2[3]:176-186) (Year: 2013).*
Official Action issued in a counterpart European Application 19 839 663.2 dated May 31, 2022.
Tyrone C. Otgaar, et al.: 37 kDa LRP::FLAG enhances telomerase activity and reduces senescent markers in vitro: Oncotarget, Oct. 7, 2017, vol. 8, (No. 49), pp. 86646-86656.
Katelyn Cuttler et al.: "Abstract", bioRxiv, Jan. 15, 2020 (Jan. 15, 2020).

(Continued)

*Primary Examiner* — Nancy J Leith
*Assistant Examiner* — Ruth Sophia Arieti
(74) *Attorney, Agent, or Firm* — LADAS & PARRY LLP

(57) ABSTRACT

LRP/LR for use in the treatment and/or prevention of Parkinson's disease (PD). Pharmaceutical compositions comprising LRP/LR for use in the treatment of Parkinson's Disease (PD), and a method of maintaining concentration levels of dopamine within a human or animal body.

3 Claims, 8 Drawing Sheets

Specification includes a Sequence Listing.

(56) References Cited

OTHER PUBLICATIONS

Stefan Weiss: “Bad Boy with a Twist: Targeting the 37 kDa/67 kDa Laminin Receptor for Treatment of Cancer and Neurodegenerative Diseases and for Changing Telomere Dynamics”, Aug. 17, 2017.
Darren J. Baker et al.: “Cellular senescence in brain aging and neurodegenerative diseases: evidence and perspectives”, Journal of Clinical Investigation: vol. 128, No. 4, Feb. 19, 2018.
Amos D Korczyn: “arkinson Drug treatment of Parkinson’s disease”, , Jan. 1, 2004 (Jan. 1, 2004), XP055675011, Retrieved from the Internet.
Chinese Office Action for copending Application No. 201980090648.3 mailed Dec. 28, 2023.
Leila Vania, etal: Patented therapeutic approaches targeting LRP/LR for cancer treatment: Expert Opinion on Therapeutic Patents: 2019, vol. 29, No. 12, 987-1009.
Ross, et al: Nature | vol. 388 | Aug. 28, 1997.
J Prev Med Chin PLA Apr. 2017 vol. 35 No. 4.
Diego A. Forero, et al.: Telomere length in Parkinson’s disease: A meta-analysis: Experimental Gerontology 75 (2016) 53-55.
Hao Wang, et al.: Telomere Length and Risk of Parkinson’s Disease: Movement Disorders, vol. 23, No. 2, 2008, pp. 302-305.
Patrick F. Chinnery, et al: No evidence of substantia nigra telomere shortening in Parkinson’s disease: Neurobiology of Aging 32, 2011, 2107.e3-2107.e5.
Diego A. Forero, et al: Telomere length in Parkinson’s disease: A meta-analysis: Experimental Gerontology 75, 2016, pp. 53-55.
Azad Farzadfard, et al: The C-terminal tail of α-synuclein protects against aggregate replication but is critical for oligomerization: Communications Biology: https://doi.org/10.1038/s42003-022-03059-8, 2022.

* cited by examiner

COMPOUNDS FOR USE IN THE TREATMENT OF PARKINSON'S DISEASE

This application is a national phase entry under 35 USC 371 of International Patent Application No.: PCT/IB2019/060302 filed on 28 Nov. 2019, which claims the benefit of ZA Application No. 2018/08025 filed on 28 Nov. 2018, the entire content of which is incorporated by reference.

FIELD OF INVENTION

The field of this invention relates to compounds for use in the treatment and/or prevention of Parkinson's disease (PD). The invention extends to pharmaceutical compositions comprising said compounds and a pharmaceutical carrier.

BACKGROUND

Parkinson's disease (PD) is the most frequent neurodegenerative disease of motor activity, with more than 10 million people worldwide suffering from the disease.

There is currently no cure for PD, but only palliative treatments that help with the management of the symptoms. These treatment options include drugs such as levodopa, dopamine and monoamine oxidase B inhibitors. The first line treatment for PD is levodopa, or L-Dopa, paired with a peripheral decarboxylase inhibitor to prevent the conversion to dopamine in the periphery. However, at high doses or prolonged use L-Dopa can cause adverse side effects such as dyskinesia, motor fluctuations and impulse control disorders.

Other non-pharmacological symptomatic therapies include functional stereotaxic neurosurgery (deep brain stimulation), physiotherapy, speech therapy and dietary alterations.

There exists a need for new and inventive compounds, pharmaceutical compositions, and/or methods to treat and/or prevent Parkinson's disease (PD).

SUMMARY

Broadly, in accordance with a first aspect of this disclosure, there is provided a 37 kDa/67 kDa laminin receptor precursor/high affinity laminin receptor (LRP/LR) and/or a fragment thereof for use in the treatment and/or prevention of Parkinson's Disease, wherein LRP/LR and/or the fragment thereof being for administration to a subject in need thereof.

In use said LRP/LR increases the C-terminal domain (CTD) of α-synuclein in the human or animal body, therein preventing aggregation thereof to ameliorate and/or treat and/or prevent PD. Increasing the CTD may also provide, in use, a concomitant decrease in cell damage and/or a maintenance of dopamine levels, therein ameliorating and/or treating and/or preventing PD.

LRP/LR may comprise a peptide/protein sequence as set forth in SEQ ID NO: 1 and/or SEQ ID NO: 2, or a fragment thereof, the fragment may be as set forth in SEQ ID NO:4 and/or SEQ ID NO:5.

LRP/LR may comprise a peptide/protein sequence having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence as set forth in SEQ ID NO: 1 or SEQ ID NO: 2.

SEQ ID NO: 1 may be a peptide/protein sequence for human LRP/LR and may have the following sequence:

```
MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTATQPEVADWSE

GVQVPSVPIQQFPTEDWSAQPATEDWSAAPTAQATEWVGATTDWS
```

SEQ ID NO: 2 may be a peptide/protein sequence for mouse (*Mus musculus*) LRP/LR and may have the following sequence:

```
MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTAAQPEVADWSE

GVQVPSVPIQQFPTEDWSAQPATEDWSAAPTAQATEWVGATTEWS
```

It is to be understood that LRP/LR is highly conserved and homologs or fragments of SEQ ID NO: 1 and SEQ ID NO: 2, and/or homologs of the fragments may also utilized in order to exercise the invention described, illustrated and/or exemplified herein.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the protein sequence of LRP/LR may form part of a larger and/or longer protein sequence.

In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide sequence that includes at least a sequence motif DYKDDDDK (SEQ ID NO: 3).

An example embodiment of a fragment of LRP/LR is exemplified as a protein/peptide having a sequence as set forth in SEQ ID NO: 4 corresponding to a fragment of SEQ ID NO:1 from amino acid residue 102 to amino acid residue 295 and/or SEQ ID NO:5 corresponding to a fragment of SEQ ID NO: 2 from amino acid residue 102 to amino acid residue 295.

SEQ ID NO: 4 may be a peptide/protein sequence for a fragment of human LRP/LR and may have the following sequence:

```
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS
```

-continued

SEQ ID NO: 5 may be a peptide/protein sequence for a fragment of mouse LRP/LR and may have the following sequence:
RFTPGTFINQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGVQVPSVPIQQFPTEDWSAQ

PATEDWSAAPTAQATEWVGATTEWS

There is provided for the peptide/protein having a sequence as set forth in SEQ ID NO: 4 and/or SEQ ID NO: 5 for use in the treatment of Parkinson's disease.

The 37 kDa/67 kDa laminin receptor precursor/high affinity laminin receptor (LRP/LR) and/or a fragment thereof may be combined with levo-dopa (or L-dopa) (or derivatives thereof) to provide composition, the composition for use in the treatment and/or prevention of Parkinson's Disease, such that in use the LRP/LRP and/or a fragment thereof facilitates maintenance of dopamine levels within the subject. The LRP/LR (or the composition) may alternatively or additionally be combined together with dopamine and/or monoamine oxidase B inhibitors for use in the treatment and/or prevention of Parkinson's disease. Maintenance of dopamine levels in the subject avoids frequent use of l-dopa and/or in turn curbs against adverse side effects associated with prolonged l-dopa usage by the subject. Further, maintenance of dopamine levels in the subject curbs against the need for continued usage of high levels of l-dopa. Consequently, relatively less l-dopa may be administered to the subject in need thereof with a concomitant longer lasting effect via the maintenance of l-dopa levels by LRP/LR. LRP/LR may also increase parkin protein levels facilitating treating and/or preventing PD. The Applicant has found this to be a significant advantage which provides for improved treatment and/or prevention protocols for Parkinson's disease.

The subject may be a human, animal, reptile, avian, amphibian or plant. Typically, the subject may be a human and/or animal, preferably human.

The LRP/LR and/or a fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous.

The Applicant was very surprised that providing LRP/LR to the human or animal body i.e. upregulating its expression increases the C-terminal domain (CTD) of α-synuclein. Providing LRP/LR as part of a treatment protocol for PD would significantly limit any chance of unwanted side effects as it is a naturally occurring protein/peptide. This would certainly ameliorate at least one of the problems known in the prior art.

In accordance with a second aspect of the invention there is provided a pharmaceutical composition comprising 37 kDa/67 kDa laminin receptor precursor/high affinity laminin receptor (LRP/LR) and/or a fragment thereof and a carrier, the pharmaceutical composition for use in the treatment of Parkinson's disease, wherein the pharmaceutical composition being for administration to a subject in need thereof.

In use said LRP/LR of the pharmaceutical composition increases the C-terminal domain (CTD) of α-synuclein in the human or animal body, therein preventing aggregation thereof to ameliorate and/or treat and/or prevent PD. Increasing the CTD may also provide, in use, a concomitant decrease in cell damage and/or a maintenance of dopamine levels, therein ameliorating and/or treating and/or preventing PD. LRP/LR may also increase parkin protein levels facilitating treating and/or preventing PD.

LRP/LR may comprise a peptide/protein sequence as set forth in SEQ ID NO: 1 or SEQ ID NO: 2, or a fragment thereof, the fragment may be as set forth in SEQ ID NO:4 and/or SEQ ID NO:5.

LRP/LR may comprise a peptide/protein sequence having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence as set forth in SEQ ID NO: 1 or SEQ ID NO: 2.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the peptide/protein sequence of LRP/LR may form part of a larger and/or longer peptide/protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide sequence that includes at least a sequence motif DYKDDDDK (SEQ ID NO: 3).

An example embodiment of a fragment of the peptide/protein sequence is exemplified as SEQ ID NO: 4 corresponding to a fragment of SEQ ID NO:1 from 102 to 295 and/or SEQ ID NO:5 corresponding to a fragment of SEQ ID NO: 2 from 102 to 295.

SEQ ID NO: 4 may be a peptide/protein sequence for a fragment of human LAP/LR and may have the following sequence:
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

SEQ ID NO: 5 may be a peptide/protein sequence for a fragment of mouse LRP/LR and may have the following sequence:
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGVQVPSVPIQQFPTEDWSAQ

PATEDWSAAPTAQATEWVGATTEWS

The pharmaceutical composition may further include levo-dopa (or L-dopa) (or derivatives thereof). In use the LRP/LRP and/or a fragment thereof facilitates maintenance of dopamine levels within the subject. Maintenance of dopamine levels in the subject avoids frequent use of l-dopa and/or in turn curbs against adverse side effects associated with prolonged l-dopa usage by the subject. Further, maintenance of dopamine levels in the subject curbs against the need for continued usage of high levels of l-dopa by the subject. The pharmaceutical composition when in use allows for relatively less l-dopa to be administered to the subject with a longer lasting effect. The pharmaceutical composition may further include dopamine and/or monoamine oxidase B inhibitors and/or excipients. In use the LRP/LRP and/or a fragment thereof facilitates increased parkin protein levels which facilitates the treatment and/or preventing of Parkinson's disease by hindering aggregation of α-synuclein. Increased parkin levels will also increase cell viability in Parkinson's Disease.

The subject may be a human, animal, reptile, avian, amphibian or plant. Typically, the subject may be a human and/or animal, preferably human.

The pharmaceutical composition may be adapted for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous.

In accordance with a third aspect of the invention there is provided a method of increasing the C-terminal domain (CTD) of α-synuclein in a cell of the human or animal body and/or a method of decreasing cell damage and/or a method of maintaining dopamine levels in the human or animal body and/or a method of increasing parkin protein levels, the method comprising the following steps:

(i) transfecting the cell to produce 37 kDa/67 kDa laminin receptor precursor/high affinity laminin receptor (LRP/LR) and/or a fragment thereof therein increasing cellular levels of LRP/LR and/or fragments thereof; or (ii) providing the cell with LRP/LR and/or fragments thereof to increase cellular levels of LRP/LR and/or fragments thereof, such that in use, said LRP/LR increases the C-terminal domain (CTD) of α-synuclein in the human or animal body, therein preventing aggregation thereof to ameliorate and/or treat and/or prevent PD, and/or such that LRP/LR decreases cell damage and/or a maintains dopamine levels of the human or animal body and/or such that the LRP/LR causes an increase in parkin protein levels/concentration, therein ameliorating and/or treating and/or preventing PD.

LRP/LR may comprise a peptide/protein sequence as set forth in SEQ ID NO: 1 or SEQ ID NO: 2, or a fragment thereof.

LRP/LR may comprise a peptide/protein sequence having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence as set forth in SEQ ID NO: 1 or SEQ ID NO: 2.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the peptide/protein sequence of LRP/LR may form part of a larger and/or longer peptide/protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide/protein sequence that includes at least a sequence motif DYKDDDDK (SEQ ID NO:3).

It is to be understood that the step of transfecting the cell to produce 37 kDa/67 kDa laminin receptor precursor/high affinity laminin receptor (LRP/LR) and/or a fragment may take place via known procedures in the art, including introduction into the cell of a transfecting agent. The step of transfecting the cell may upregulate LRP/LR.

An example embodiment of a fragment of the peptide/protein sequence is exemplified as SEQ ID NO: 4 corresponding to a fragment of SEQ ID NO:1 from 102 to 295 and/or SEQ ID NO:5 corresponding to a fragment of SEQ ID NO: 2 from 102 to 295.

```
SEQ ID NO: 4 may be a peptide/protein sequence for
a fragment of human LRP/LR and may have the
following sequence:
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

SEQ ID NO: 5 may be a peptide/protein sequence for
a fragment of mouse LRP/LR and may have the
following sequence:
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGVQVPSVPIQQFPTEDWSAQ

PATEDWSAAPTAQATEWVGATTEWS.
```

The subject may be a human, animal, reptile, avian, amphibian or plant. Typically, the subject may be a human and/or animal, preferably human.

The LRP/LR and/or a fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous. Alternatively and/or additionally, the transfecting agent may be formulated into a pharmaceutical composition, wherein the pharmaceutical composition may further include a pharmaceutical carrier for parenteral or non-parenteral administration to the subject.

The method of maintaining dopamine levels in the human or animal body may further include the step of providing l-dopa (or levo dopa) to the subject in combination with LRP/LR or a fragment thereof. In use the LRP/LRP and/or a fragment thereof facilitates maintenance of dopamine levels within the subject. Maintenance of dopamine levels in the subject avoids frequent use of l-dopa and/or in turn curbs against adverse side effects associated with prolonged l-dopa usage by the subject. Further, maintenance of dopamine levels in the subject curbs against the need for continued usage of high levels of l-dopa.

The method allows for relatively less l-dopa to be administered to the subject with a longer lasting effect. The combination of LRP/LR and/or a fragment thereof and l-dopa may be formulated as a pharmaceutical composition for administration to the subject in need thereof. The method may further include the steps of providing dopamine and/or monoamine oxidase B inhibitors to the subject.

In accordance with a fourth aspect of the invention there is provided a method of treating and/or preventing Parkinson's disease, the method comprising the step of administering to a subject in need thereof 37 kDa/67 kDa laminin receptor precursor/high affinity laminin receptor (LRP/LR) and/or a fragment thereof, such that in use the LRP/LR and/or the fragment thereof increases the C-terminal domain (CTD) of α-synuclein in the human or animal body, therein preventing aggregation thereof to ameliorate and/or treat and/or prevent PD, and/or, such that LRP/LR decreases cell damage and/or a maintains dopamine levels of the human or animal body, and/or such that LRP/LR increases parkin protein levels therein ameliorating and/or treating and/or preventing PD.

LRP/LR may comprise a peptide/protein sequence as set forth in SEQ ID NO: 1 or SEQ ID NO: 2, or a fragment thereof.

LRP/LR may comprise a peptide/protein sequence having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence as set forth in SEQ ID NO: 1 or SEQ ID NO: 2.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the peptide/protein sequence of LRP/LR may form part of a larger and/or longer peptide/protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide/protein sequence that includes at least a sequence motif DYKDDDDK (SEQ ID NO: 3).

An example embodiment of a fragment of the peptide/protein sequence is exemplified as SEQ ID NO: 4 corresponding to a fragment of SEQ ID NO: 1 from 102 to 295 and/or SEQ ID NO:5 corresponding to a fragment of SEQ ID NO: 2 from 102 to 295.

```
SEQ ID NO: 4 may be a peptide/protein sequence for
a fragment human LRP/LR and may have the
following sequence:
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS
```

-continued

```
SEQ ID NO: 5 may be a peptide protein sequence for
a fragment of mouse LRP/LR and may have the
following sequence:
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGVQVPSVPIQQFPTEDWSAQ

PATEDWSAAPTAQATEWVGATTEWS
```

The method of treating and/or preventing Parkinson's disease may further include the step of administering to the subject l-dopa (or levo dopa) to the subject. This step may take place concomitantly with, or in addition to, the step of administering to the subject in need thereof 37 kDa/67 kDa laminin receptor precursor/high affinity laminin receptor (LRP/LR) and/or a fragment thereof. In use the LRP/LRP and/or a fragment thereof facilitates maintenance of dopamine levels within the subject typically when administrated concomitantly with, or in addition to, administration of l-dopa. Maintenance of dopamine levels in the subject avoids frequent use of l-dopa and/or in turn curbs against adverse side effects associated with prolonged l-dopa usage by the subject.

The subject may be a human, animal, reptile, avian, amphibian or plant. Typically, the subject may be a human and/or animal, preferably human.

The LRP/LR and/or a fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration.

Typically, non-parenteral administration may be oral. Parenteral administration may include at least one of intravenous, subcutaneous and intramuscular administration. Typically, parenteral administration may be intravenous. The combination of LRP/LR and/or a fragment thereof and l-dopa may be formulated as a pharmaceutical composition for administration to the subject in need thereof. The pharmaceutical composition may further include dopamine and/or monoamine oxidase B inhibitors and/or excipients.

Broadly, in accordance with a fifth aspect of this disclosure, there is provided a 37 kDa/67 kDa laminin receptor precursor/high affinity laminin receptor (LR P/LR) and/or a fragment thereof for use in the treatment of wounds, wherein LRP/LR and/or the fragment thereof being for administration to a subject in need thereof. The wounds may be external skin lesions. The wound may be internal lesions and/or damage to internal organs inside a human or animal body.

LRP/LR may comprise a peptide/protein sequence as set forth in SEQ ID NO: 1 and/or SEQ ID NO: 2, or a fragment thereof as set forth in SEQ ID NO:4 and/or SEQ ID NO: 5.

LRP/LR may comprise a peptide/protein sequence having at least 80% homology to the sequences as set forth in SEQ ID NO: 1 or SEQ ID NO: 2, or a fragment thereof.

LRP/LR may comprise homologs or fragments thereof, and homologs of the fragments, wherein LRP/LR may comprise a peptide/protein sequence as set forth in SEQ ID NO: 1 or SEQ ID NO: 2.

SEQ ID NO: 1 may be a peptide/protein sequence for human LRP/LR and may have the following sequence:
MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTATQPEVADWS

EGVQVPSVPIQQFPTEDWSAQPATEDWSAAPTAQATEWVGATTDWS

SEQ ID NO: 2 may be a peptide/protein sequence for mouse (*Mus musculus*) LRP/LR and may have the following sequence:
MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLARAEVLRMRGTISREHPWEVMP

DLYFYRDPEEIEKEEQAAAEKAVTKEEFQGEWTAPAPEFTAAQPEVADWS

EGVQVPSVPIQQFPTEDWSAQPATEDWSAAPTAQATEWVGATTEWS

It is to be understood that LRP/LR is highly conserved and homologs or fragments of SEQ ID NO: 1 and SEQ ID NO: 2, and/or homologs of the fragments may also utilized in order to exercise the invention described, illustrated and/or exemplified herein.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the protein sequence of LRP/LR may form part of a larger and/or longer protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide sequence that includes at least a sequence motif DYKDDDDK (SEQ ID NO: 3).

An example embodiment of a fragment of LRP/LR is exemplified as a protein/peptide having a sequence as set forth in SEQ ID NO: 4 corresponding to a fragment of SEQ ID NO:1 from amino acid residue 102 to amino acid residue 295 and/or SEQ ID NO:5 corresponding to a fragment of SEQ ID NO: 2 from amino acid residue 102 to amino acid residue 295.

SEQ ID NO: 4 may be a peptide/protein sequence for a fragment of human LRP/LR and may have the following sequence:
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

-continued

SEQ ID NO: 5 may be a peptide/protein sequence for a fragment of mouse LRP/LR and may have the following sequence:
RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTAAQPEVADWSEGAVQVPSVPIQQFPTEDWSA

QPATEDWSAAPTAQATEWVGATTEWS

There is provided for the peptide/protein having a sequence as set forth in SEQ ID NO: 4 and/or SEQ ID NO: 5 for use in the treatment of wounds, preferably external skin lesions in the human or animal body.

The subject may be a human and/or animal, preferably human.

The LRP/LR and/or a fragment thereof may be formulated into a pharmaceutical composition, which pharmaceutical composition may further include a pharmaceutical carrier for parenteral or non-parenteral administration to the subject. Non-parenteral administration may include at least one of, but not limited to, the following group: oral, nasal, rectal, vaginal, optical and transdermal administration.

Typically, non-parenteral administration may be oral. Parenteral administration may include at least one of intravenous, subcutaneous and intramuscular administration. Typically, parenteral administration may be intravenous.

Typically, the composition is formulated for topical administration to an external skin lesion in a human and/or animal body. Such a topical administration may be, but is not limited to, an ointment, cream, gel, lotion, liquid, bandage, plaster, cast, and/or a combination of the aforementioned.

There is further provided for 37 kDa/67 kDa laminin receptor precursor/high affinity laminin receptor (LRP/LR) and/or a fragment thereof for use in the treatment of Parkinson's disease, substantially as herein described, illustrated and/or exemplified with reference to any one of the examples and/or figures.

There is further provided for a pharmaceutical composition substantially as herein described, illustrated and/or exemplified with reference to any one of the examples and/or figures.

There is further provided for a method of increasing the C-terminal domain (CTD) of α-synuclein in the human or animal body and/or a method of decreasing cell damage and/or a method of maintaining dopamine levels in the human or animal body, the method(s) substantially as herein described, illustrated and/or exemplified with reference to any one of the examples and/or figures.

BRIEF DESCRIPTION OF THE DRAWINGS

Embodiments of the disclosure will be described below by way of example only and with reference to the accompanying drawings in which.

Figure 4A:
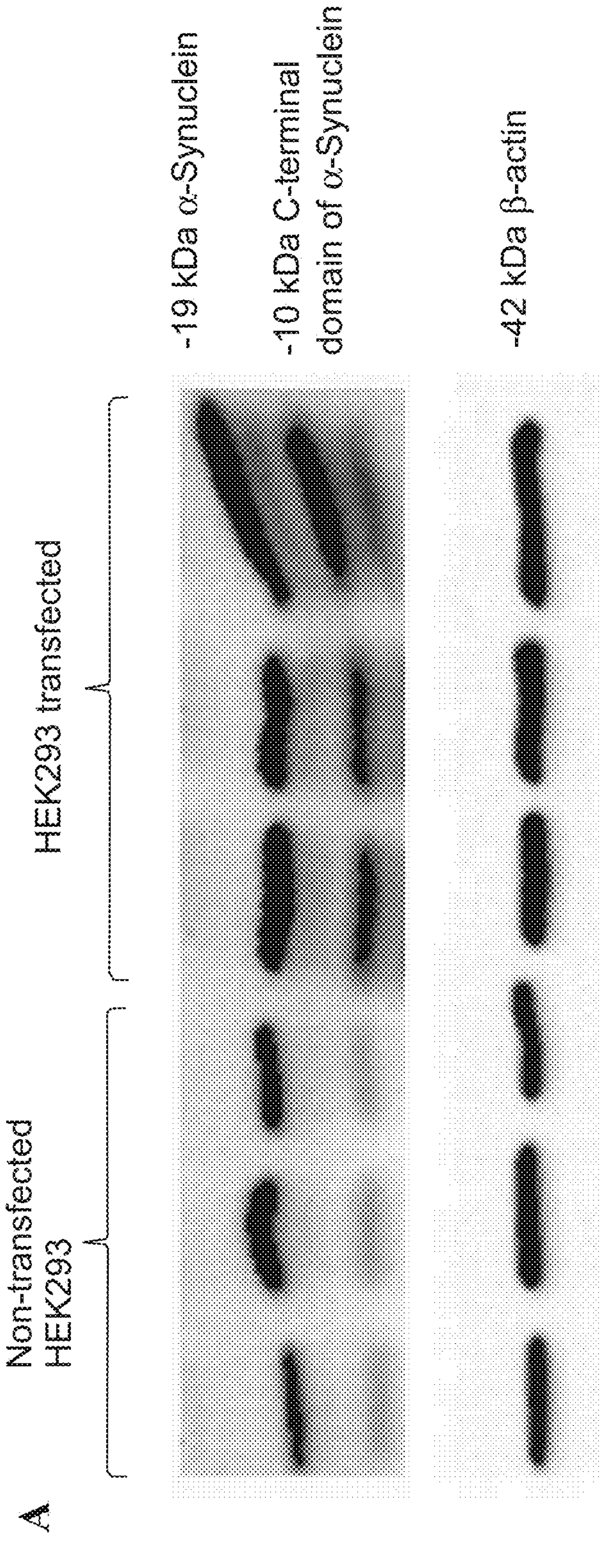

Densitometric analysis was performed followed by statistical analysis using the student's t-test. Densitometric and statistical analysis revealed that pCIneo-LRP::FLAG transfections resulted in an increase of total LRP levels by 71.24%;

FIG. 3A to N shows confocal microscopy at 630× magnification indicating expression levels and localisation of LRP and α-synuclein;

FIGS. 4A and B show Western blot and densitometric analysis of protein lysates.

Figure 5:
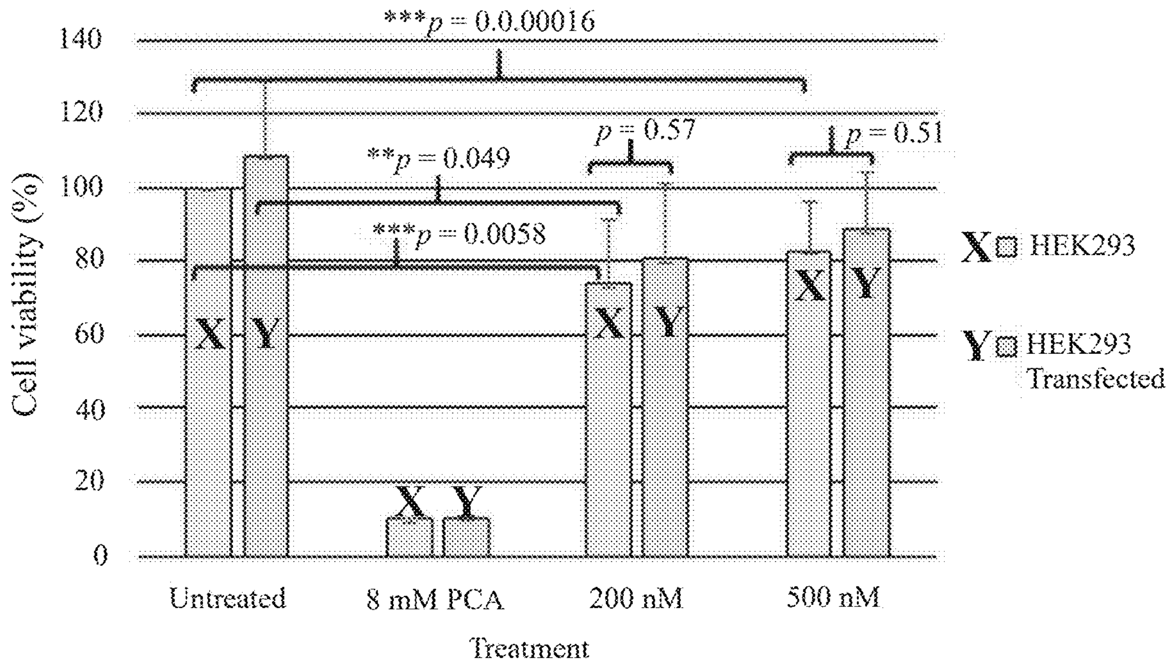
Figure 6:
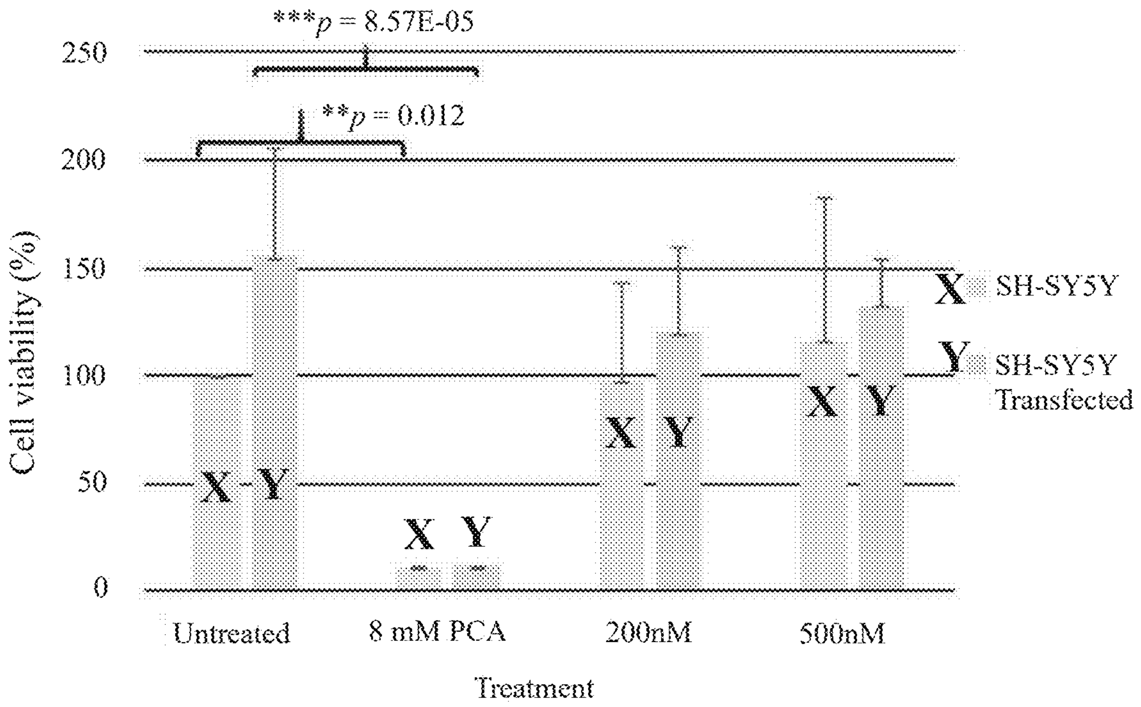
Figure 7:
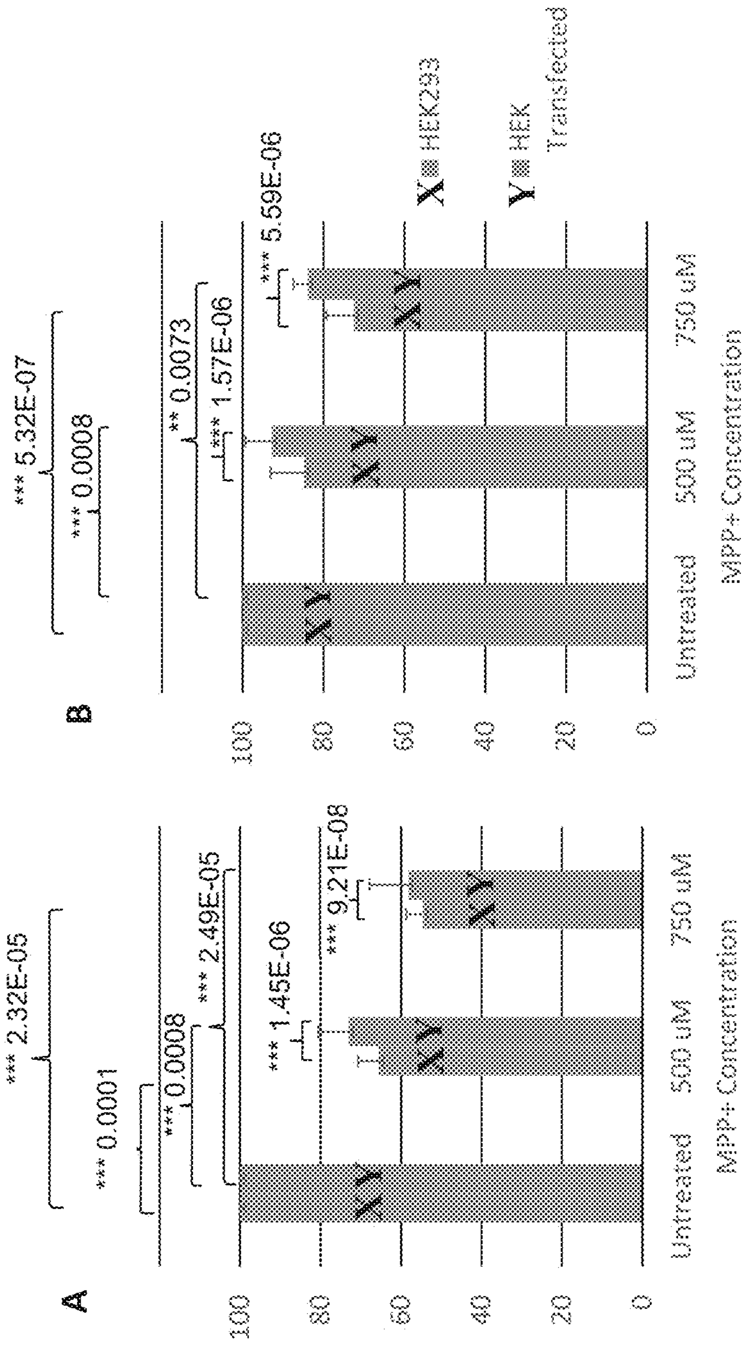
Figure 8:
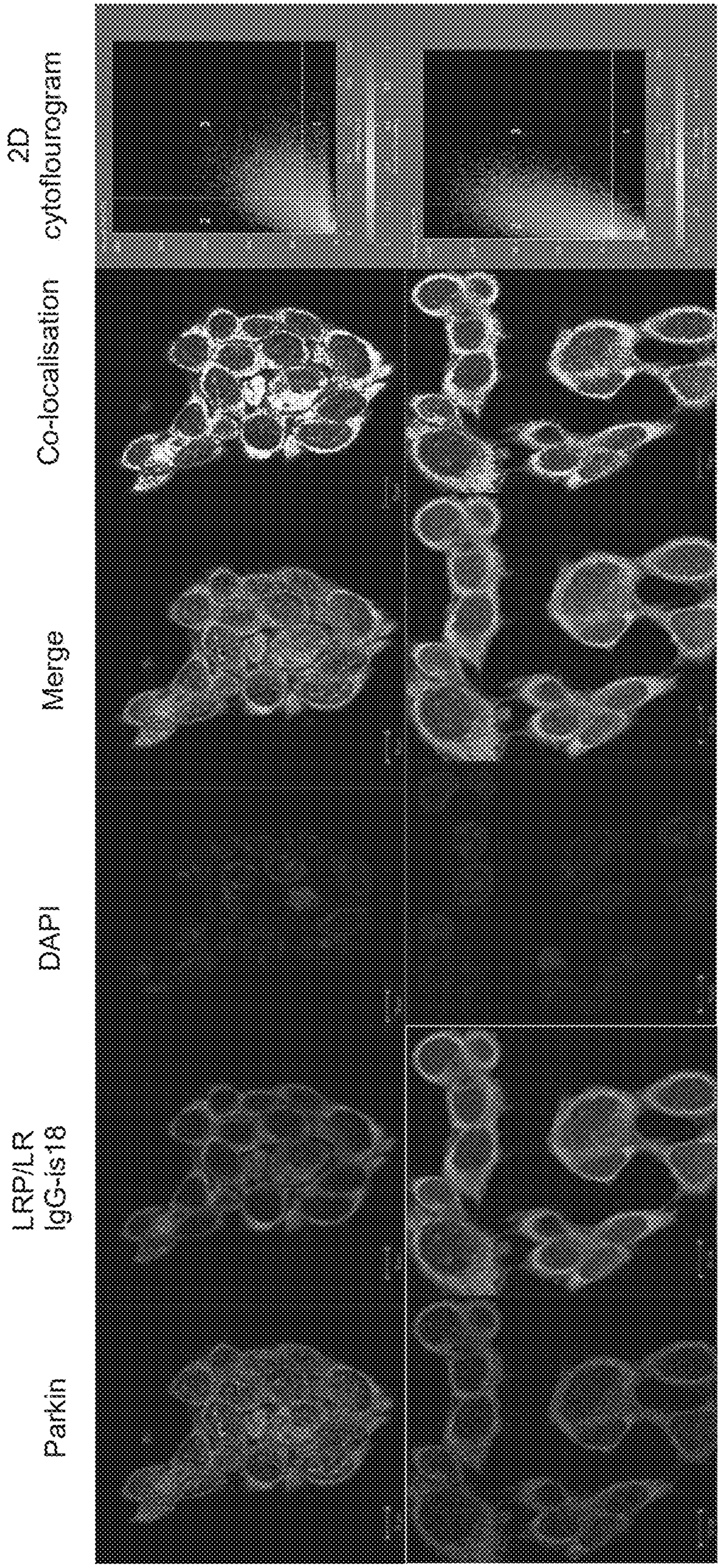

Western blot analysis was performed on pCIneo-LRP::FLAG transfected HEK293 and non-transfected HEK293 cells. Primary antibody used were raised against α-Synuclein. Secondary antibodies were coupled with HRP. A HRP coupled primary antibody was used to detect β-actin. pCIneo-LRP::FLAG transfections resulted in an increase of C-terminal domain levels of α-synuclein LRP::FLAG overexpression and increase of total LRP levels. Densitometric analysis was performed followed by statistical analysis using the student's t-test. Densitometric and statistical analysis revealed that pCIneo-LRP::FLAG transfections resulted in a significant increase C-terminal domain levels of α-synuclein by 165.22%;

FIG. 5 shows MTT assay analysis of LRP::FLAG transfected and non-transfected HEK293 cells indicating an increase in cell viability in LRP::FLAG overexpressing HEK293 cells in the presence of 200 nM and 500 nM recombinant α-Synuclein in comparison to non-transfected HEK293 cells;

FIG. 6 shows MTT assay analysis in LRP::FLAG transfected and non-transfected SH-SY5Y cells indicating an increase in cell viability in LRP::FLAG overexpressing SH-SY5Y cells in the presence of 200 nM and 500 nM recombinant α-Synuclein compared to non-transfected SH-SY5Y cells;

FIGS. 7A and B shows MTT assay analysis of pCIneo-moLRP::FLAG transfected and non-transfected HEK293 cells indicating a significant increase in cell viability in LRP::FLAG overexpressing HEK293 cells in the presence of 500 uM and 750 nM 1-Methyl-4-phenylpyridinium iodide (MPP+) for (A) 48 hours and (B) 72 hours; and FIG. 8 shows confocal microscopy at 630× magnification indicating expression levels and localization of LRP and parkin. Primary antibodies used were raised against LRP, parkin and hTERT. Secondary antibodies were coupled with FITC, Cy3 and Alexaflour 647. Panels A to F represent DLD-1 cells while panels G to L represent DLD-1 cells that have been transfected with the pCIneo-LRP::FLAG plasmid. Panel A and G represent parkin in yellow and panel B and H represent LRP/LR in green. Panel D and I represent a merge of parkin and LRP/LR. Panel E and K represents the colocalization of the two proteins, where the white indicates an overlap and possible interaction between parkin and LRP/LR. Colocalization occurs intracellularly as indicated by the diagonal in the 2D cytofluorogram graphs (F) with with 59/6 of parkin colocalizing with 54% of LRP/LR in DLD-1 cells while in DLD-1 cells overexpressing LRP::FLAG 99% of parkin colocalizes with 22% of LRP.

DETAILED DESCRIPTION OF THE INVENTION

The Summary herein above is repeated here by way of reference thereto and is not fully repeated to avoid lengthy repetition.

Figure 1:
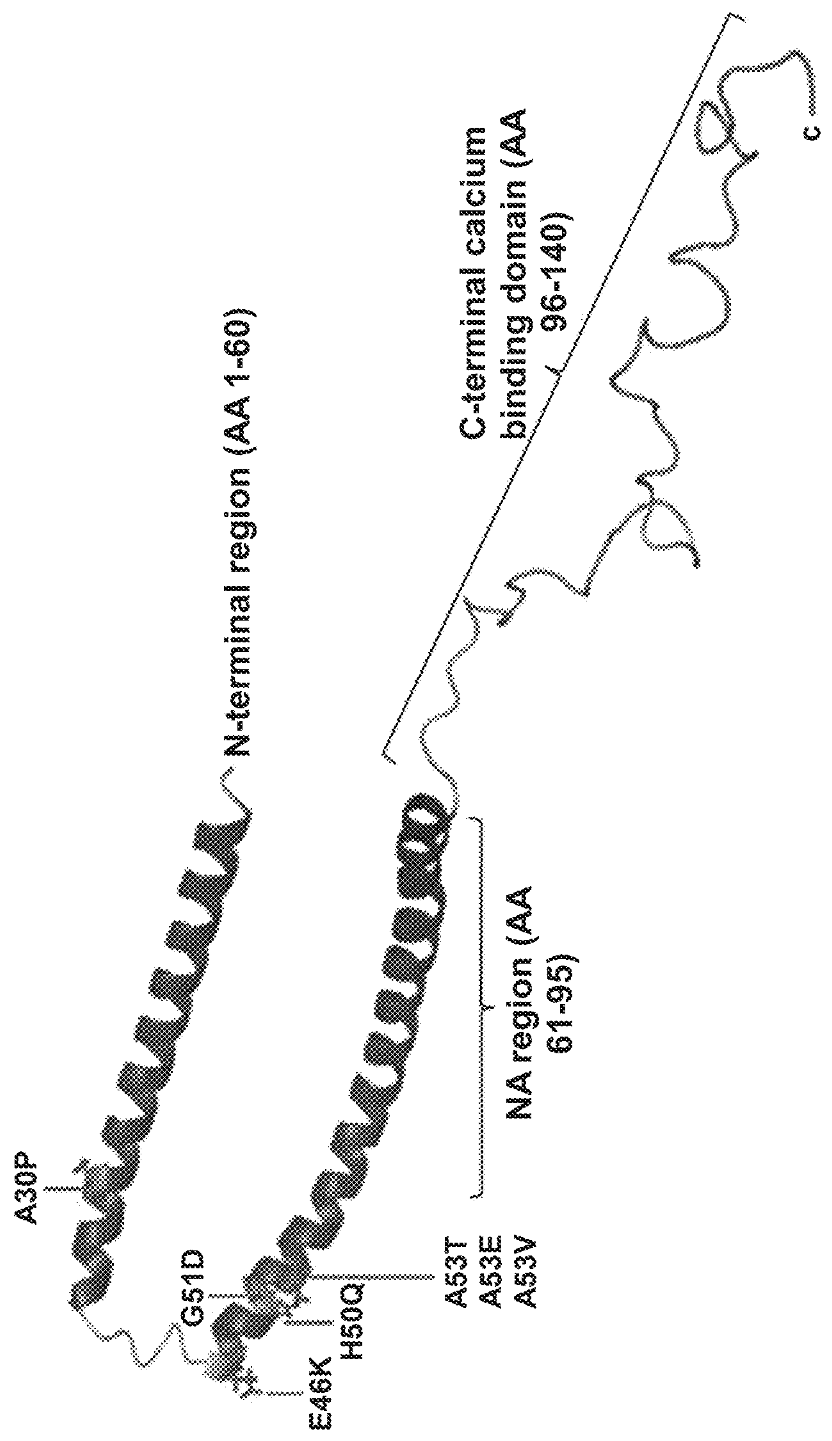
FIG. 1 shows the full-length structure of alpha (α)-synuclein.

Parkinson's disease (PD) is the most frequent neurodegenerative disease of motor activity, with more than 10 million people worldwide suffering from the disease. α-synuclein is implicated in PD and is encoded by the gene SNCA. In PD, α-synuclein forms aggregates and is the primary constituent of Lewy bodies. Mutations in the SNCA gene result in the aggregation of α-synuclein and thus the familial form of Parkinson's disease. The C-terminal domain (CTD) of α-synuclein prevents the aggregation of α-synuclein (refer FIG. 1).

LRP/LR is a multifunctional receptor protein that plays a vital role in the pathogenesis of neurodegenerative disorders including Alzheimer's disease and prion disorders. It has previously been shown that a knock-down (down regulation) of LRP/LR is a useful treatment protocol for Alzheimer's disease as per the disclosures of PCT/IB2012/054968.

In contrast, and surprisingly to the Applicant, an overexpression of LRP/LR is now found to be a beneficial treatment protocol in the treatment of Parkinson's disease (PD). This was completely unexpected given previous findings. Without being limited to theory, this indicates the complex and unpredictable nature of biochemical pathways involved in neurodegenerative disorders, particularly PD.

The diagnosis of PD relies on the observation of the characteristics of the disease, described above, as there are no specific tests available to diagnose PD. Non-motor symptoms are used to diagnose the disease in the early stages as they are more prominent. There is currently no cure for PD, but only palliative treatments that help with the management of the symptoms. These treatment options include drugs such as levodopa, dopamine and monoamine oxidase B inhibitors. The first line treatment for PD is levodopa, or L-Dopa, paired with a peripheral decarboxylase inhibitor to prevent the conversion to dopamine in the periphery. However, at high doses or prolonged use L-Dopa can cause adverse side effects such as dyskinesia, motor fluctuations and impulse control disorders. Other non-pharmacological symptomatic therapies include functional stereotaxic neurosurgery (deep brain stimulation), physiotherapy, speech therapy and dietary alterations. New compounds for use in the treatment of PD are desired.

PD is primarily defined by the loss of dopamine-producing neurons located in the substantia nigra pars compacta (SNPC) and is ultimately responsible for the prominent motor features of PD (Dexter & Jenner, 2013). The loss of these dopamine-producing neurons located in the SNPC not only results in organ shrinkage, but it also results in the presence of Lewy bodies (Dauer & Prezedborski, 2003). Lewy bodies are intraneuronal proteinaceous inclusions that consist of more than 76 different components (Wakabayashi et al., 2007). Motor and sleep regulation are two of the main functions of the SNPC and thus a loss of these neurons leads to dysregulation of these and other functions of the SNPC (Lima et al., 2009). Oxidative toxins that are released during oxidative stress by glial cells may also result in neuronal cell death in PD (Jenner, 2003).

Sporadic forms of PD comprise 90% of the total PD cases (Yasuda & Mochizuki, 2010) and can be caused by unknown degenerative disease processes, toxins, metabolic disturbances or drugs (Dickson, 2012). Only a few cases of PD are familial and are due to mutations in the genes that encode the proteins, α-Synuclein and parkin (Yasuda & Mochizuki, 2010). α-Synuclein is the primary constituent of Lewy bodies and is encoded by the gene SNCA (Yasuda & Mochizuki, 2010). Mutations in the SNCA gene result in the aggregation of α-Synuclein and thus the familial form of PD (Yasuda & Mochizuki, 2010). Parkin is an E3 ubiquitin ligase that is involved in ubiquitin-mediated degradation of proteins (Seirafi et al., 2015). The PARK2 gene encodes the protein parkin and mutations in this gene results in the loss-of-function of the protein parkin (Kitada et al., 1998). Parkin is responsible for the ubiquitination of O-glycosylated forms of α-Synuclein and thus the loss-of-function of parkin results in the aggregation of α-Synuclein (Shimura et al., 2000). Yang et al., (2003) demonstrated that overexpression of parkin reduced the toxicity of α-Synuclein and thus protects the cells from the devastating effects of α-Synuclein (Yang et al., 2003).

The 19 kDa protein, α-Synuclein, does not have a defined structure in aqueous solution (Stefanis et al., 2012). α-Synuclein is found, predominantly, in neuronal cells in the synaptic vesicles as well as in the nucleus (Auluck et al., 2010). The protein is made up of an CTD (CTD), the non-amyloid-0 component of plaques (NAC) domain and the NTD (NTD) (Xu & Pu, 2016). The NTD is involved in membrane binding (Vamvaca et al., 2009). The NAC domain is the domain responsible for aggregation (Rajagopalan et al., 2001) and the CTD interacts with the NAC domain to inhibit the aggregation (Emamzadeh, 2016). The NAC region of α-Synuclein is also a constituent of the plaques found in Alzheimer's disease (AD) (Bendor et al., 2013). α-Synuclein has a number of functions including neuronal differentiation through the ERK/MAPK pathway (Fu et al., 2000) resulting in the downregulation of dopamine biosynthesis through the inhibition of tyrosine hydroxylase (Rodriguez-Araujo et al., 2015).

The main constituent of Lewy bodies is the fibrillar form of α-Synuclein which is as a result of mutations and replications (Dolgacheva et at., 2018). Patients suffering from PD also have high levels of phosphorylated and nitrated forms of α-Synuclein, which could be indicating that these post-translational modifications could be promoting aggregation of α-Synuclein and thus PD (Rocha et al., 2018). Dysfunctional lysosomal clearance and mutated lysosomal hydrolase favour α-Synuclein aggregation and thus these individuals have a higher chance of developing PD (Sidransky et al., 2009).

Dysregulation of the autophagy-lysosomal pathway (ALP) as well as the ubiquitin-proteasome system (UPS) favours α-Synuclein aggregation as these systems are result in the degradation of α-Synuclein (Rocha et al., 2018). Recent studies have also demonstrated that CTD truncation favours aggregation of α-Synuclein (van der Wateren et al., 2018).

Herein below the Applicant shows that human embryonic kidney (HEK293) cells were stably transfected with pCIneo-LRP::FLAG which resulted in successful LRP::FLAG overexpression. LRP::FLAG overexpression resulted in (i) increased α-synuclein protein levels (ii) colocalization between α-synuclein and LRP/LR, (iiii) colocalization between LRP/LR and parkin, and (iv) increased cell viability LRP::FLAG overexpression HEK293 cells in the presence of MPP+(a Parkinson's disease inducer).

Western blot analysis, revealed significant increased levels of the CTD of α-synuclein post LRP::FLAG overexpression. MTT assays following treatment with recombinant α-synuclein revealed an increase in cell viability of LRP::FLAG transfected HEK293 and SH-SY5Y cells compared to non-transfected cells. Without being limited to theory, the Applicant provides LRP/LR for use in treating and/or preventing PD, wherein LRP/LR is for administration to a human or animal in need thereof, and wherein said LRP/LR increases the C-terminal domain (CTD) of α-synuclein, therein preventing aggregation thereof to ameliorate PD.

Increasing the CTD also provides, in use, a concomitant decrease in cell damage and/or a maintenance of dopamine levels. The maintenance of dopamine levels in the subject curbs against the need for continued usage of high levels of l-dopa as a treatment protocol for Parkinson's disease. Consequently, relatively less l-dopa may be administered to the subject in need thereof with a concomitant longer lasting effect via the maintenance of l-dopa levels by LRP/LR. LRP/LR is also shown to increase cell viability. The Applicant has found this to be a significant advantage which provides for improved treatment and/or prevention protocols for Parkinson's disease.

MTT assay analysis of pCIneo-moLRP::FLAG transfected and non-transfected HEK293 cells indicating a significant increase in cell viability in LRP::FLAG overexpressing HEK293 cells in the presence of 500 uM and 750 nM 1-Methyl-4-phenylpyridinium iodide (MPP+), a PD inducer, as shown in FIGS. 7A and 7B. Increased parkin levels facilitated by overexpression of LRP/LR may further provide for maintaining α-synuclein levels and/or curbs or hinders aggregation of α-synuclein levels.

In accordance with a first aspect of the invention there is provided a 37 kDa/67 kDa laminin receptor precursor/high affinity laminin receptor (LRP/LR) and/or a fragment thereof for use in the treatment and/or prevention of Parkinson's disease, wherein LRP/LR and/or the fragment thereof being for administration to a subject in need thereof. The LRP/LR may comprise a peptide/protein sequence as set forth in SEQ ID NO: 1 or SEQ ID NO: 2, or a fragment thereof, such as the fragment having a sequence as set forth in SEQ ID NO:4 and/or SEQ ID NO:5. Alternatively and/or additionally, the LRP/LR may comprise a peptide/protein sequence having at least 80/a homology to the sequences as set forth in SEQ ID NO: 1 or SEQ ID NO: 2 or SEQ ID NO: 4 or SEQ ID NO:5, or a fragment thereof. Further still, the LRP/LR may comprise homologs or fragments thereof, and homologs of the fragments, wherein LRP/LR may comprise a peptide/protein sequence as set forth in SEQ ID NO: 1 or SEQ ID NO: 2 or SEQ ID NO: 4 or SEQ ID NO:5.

In use said LRP/LR increases the C-terminal domain (CTD) of α-synuclein in the human or animal body, therein preventing aggregation thereof to ameliorate and/or treat and/or prevent PD. Increasing the CTD may also provide, in use, a concomitant decrease in cell damage and/or a maintenance of dopamine levels, therein ameliorating and/or treating and/or preventing PD. LRP/LR may be combined with levo-dopa (l-dopa) for use in treating and/or preventing PD wherein the LRP/LR facilitates maintenance of dopamine levels therein requiring less l-dopa and curbing against the negative side effects of high l-dopa usage and/or continued l-dopa usage. Increased parkin levels facilitated by overexpression of LRP/LR may further provide for maintaining α-synuclein levels and/or curbs or hinders aggregation of α-synuclein levels.

```
SEQ ID NO: 1 may be a peptide/protein sequence for
human LRP/LR and may have the following sequence:
MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD
```

-continued

LYFYRDPEEIEKEEQAAAEKAVTKEEFQGEWTAPAPEFTATQPEVADWSE

GVQVPSVPIQQFPTEDWSAQPATEDWSAAPTAQATEWVGATTDWS

SEQ ID NO: 2 may be a peptide/protein sequence for mouse (*Mus musculus*) LRP/LR and may have the following sequence:

MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTAAQPEVADWSE

GVQVPSVPIQQFPTEDWSAQPATEDWSAAPTAQATEWVGATTEWS

It is to be understood that LRP/LR is highly conserved and homologs or fragments of SEQ ID NO: 1 and SEQ ID NO: 2, and/or homologs of the fragments may also utilized in order to exercise the invention described, illustrated and/or exemplified herein.

The peptide/protein sequence of LRP/LR or a homolog or fragment thereof, or a homolog of the fragment, may be bound to, or bonded with, or joined to, or conjugated with, or associated with, an additional protein sequence, amino acid sequence, peptide, protein, or antibody. Alternatively and/or additionally, the peptide/protein sequence of LRP/LR may form part of a larger and/or longer protein sequence. In a certain embodiment of the invention LRP/LR may be may be bound to, or bonded with, or joined to, or conjugated with, or associated with, FLAG protein, such that in use, the LRP/LR may be tagged with FLAG. FLAG protein may include a peptide/protein sequence that includes at least a sequence motif DYKDDDDK (SEQ ID NO: 3). FLAG is used to aid in evaluation and/or quantification and/or interpretation of the experiments below in the Examples section. Although used in the Examples, it is not necessary in order to exercise the claimed invention. However, a person skilled in the art may want to include a tag such as FLAG.

An example embodiment of a fragment of LRP/LR is exemplified as a protein/peptide having a sequence as set forth in SEQ ID NO: 4 corresponding to a fragment of SEQ ID NO: 1 from amino acid residue 102 to amino acid residue 295 and/or SEQ ID NO:5 corresponding to a fragment of SEQ ID NO: 2 from amino acid residue 102 to amino acid residue 295.

SEQ ID NO: 4 may be a peptide/protein sequence for a fragment of human LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

AVTKEEFQGEWTAPAPEFTATQPEVADWSEGVQVPSVPIQQFPTEDWSAQ

PATEDWSAAPTAQATEWVGATTDWS

SEQ ID NO: 5 may be a peptide/protein sequence for a fragment of mouse LRP/LR and may have the following sequence:

RFTPGTFTNQIQAAFREPR

LLVVTDPRADHQPLTEASYVNLPTIALCNTDSPLRYVDIAIPCNNKGAHS

VGLMWWMLAREVLRMRGTISREHPWEVMPDLYFYRDPEEIEKEEQAAAEK

-continued

AVTKEEFQGEWTAPAPEFTAAQPEVADWSEGVQVPSVPIQQFPTEDWSAQ

PATEDWSAAPTAQATEWVGATTEWS.

The LRP/LR and/or a fragment thereof may be formulated into a pharmaceutical composition, which pharmaceutical composition may further include a pharmaceutical carrier for parenteral or non-parenteral administration to the subject.

Non-parenteral administration may include at least one of, but not limited to, the following group: oral, nasal, rectal, vaginal, optical and transdermal administration. Typically, non-parenteral administration may be oral. Parenteral administration may include at least one of intravenous, subcutaneous and intramuscular administration. Typically, parenteral administration may be intravenous. The pharmaceutical composition may further include l-dopa. The pharmaceutical composition may further include dopamine and/or monoamine oxidase B inhibitors and/or excipients.

In accordance with a second aspect of the invention there is provided a pharmaceutical composition comprising 37 kDa/67 kDa laminin receptor precursor/high affinity laminin receptor (LRP/LR) and/or a fragment thereof and a carrier, the pharmaceutical composition for use in the treatment and/or prevention of Parkinson's disease, wherein the pharmaceutical composition being for administration to a subject in need thereof. The pharmaceutical composition may also include levo dopa (l-dopa). The pharmaceutical composition may further include dopamine and/or monoamine oxidase B inhibitors and/or excipients.

In accordance with a third aspect of the invention there is provided a method of increasing the C-terminal domain (CTD) of α-synuclein in the human or animal body and/or a method of decreasing cell damage and/or a method of maintaining dopamine levels in the human or animal body and/or a method of increasing parking protein levels, the method comprising the following steps:

(i) transfecting the cell to produce 37 kDa/67 kDa laminin receptor precursor/high affinity laminin receptor (LRP/LR) and/or a fragment thereof therein increasing cellular levels of LRP/LR and/or fragments thereof; or
(ii) providing the cell with LRP/LR and/or fragments thereof to increase cellular levels of LRP/LR and/or fragments thereof, such that in use, said LRP/LR increases the C-terminal domain (CTD) of α-synuclein in the human or animal body, therein preventing aggregation thereof to ameliorate and/or treat and/or prevent PD, and/or such that LRP/LR decreases cell damage and/or a maintains dopamine levels of the human or animal body and/or such that the LRP/LR increases parkin protein levels/concentration, therein ameliorating and/or treating and/or preventing PD.

It is to be understood that the step of transfecting the cell to produce 37 kDa/67 kDa laminin receptor precursor/high affinity laminin receptor (LRP/LR) and/or a fragment may take place via known procedures in the art, including introduction into the cell of a transfecting agent.

The method of maintaining dopamine levels in the human or animal body may further include the step of providing l-dopa (or levo dopa) to the subject in combination with LRP/LR or a fragment thereof. In use the LRP/LRP and/or a fragment thereof facilitates maintenance of dopamine levels within the subject. Maintenance of dopamine levels in the subject avoids frequent use of l-dopa and/or in turn curbs against adverse side effects associated with prolonged l-dopa usage by the subject. Further, maintenance of dopamine levels in the subject curbs against the need for continued usage of high levels of l-dopa. The method allows for relatively less l-dopa to be administered to the subject with a longer lasting effect. The combination of LRP/LR and/or a fragment thereof and l-dopa may be formulated as a pharmaceutical composition for administration to the subject in need thereof. The method may further include the steps of providing dopamine and/or monoamine oxidase B inhibitors to the subject.

In accordance with a fourth aspect of the invention there is provided a method of treating and/or preventing Parkinson's disease, the method comprising the step of administering to a subject in need thereof 37 kDa/67 kDa laminin receptor precursor/high affinity laminin receptor (LRP/LR) and/or a fragment thereof.

In use said LRP/LR increases the C-terminal domain (CTD) of α-synuclein in the human or animal body, therein preventing aggregation thereof to ameliorate and/or treat and/or prevent PD. Increasing the CTD may also provide, in use, a concomitant decrease in cell damage and/or a maintenance of dopamine levels, therein ameliorating and/or treating and/or preventing PD. The method may further include the steps of providing levo dopa (l-dopa) and/or dopamine and/or monoamine oxidase B inhibitors to the subject.

In accordance with a fifth aspect of the invention there is provided a 37 kDa/67 kDa laminin receptor precursor/high affinity laminin receptor (LRP/LR) and/or a fragment thereof for use in the treatment of wounds, wherein LRP/LR and/or the fragment thereof being for administration to a subject in need thereof. The LRP/LR may comprise a peptide/protein sequence as set forth in SEQ ID NO: 1 or SEQ ID NO: 2, or a fragment thereof, such as the fragment having a sequence as set forth in SEQ ID NO: 4 and/or SEQ ID NO: 5. Alternatively and/or additionally, the LRP/LR may comprise a peptide/protein sequence having at least 80% homology to the sequences as set forth in SEQ ID NO: 1 or SEQ ID NO: 2 or SEQ ID NO: 4 or SEQ ID NO: 5, or a fragment thereof. Further still, the LRP/LR may comprise homologs or fragments thereof, and homologs of the fragments, wherein LRP/LR may comprise a peptide/protein sequence as set forth in SEQ ID NO: 1 or SEQ ID NO: 2 or SEQ ID NO: 4 or SEQ ID NO: 5. The wounds are preferably skin lesions, but may be wounds to internal organs.

Specific, but non-limiting embodiments of the invention will now be described. The Applicant envisages conducting further work including but not limited to in vivo and in vitro experiments.

EXAMPLES

The Examples here below serve to further exemplify the invention and are non-limiting in their scope.

Example 1—Compounds for Use in the Impediment of Parkinson's Disease

List of Abbreviations

AD Alzheimer's disease
ALP Autophagy-lysosomal pathway
BCA Bicinchoninic acid
BSA Bovine serum album
CTD C-terminal domain
DAPI Diamidino-2-phenylindole
DLD-1 late stage colorectal carcinoma cells
DMEM Dulbecco's modified eagle medium
DMSO Dimethyl sulfoxide
EDTA Ethylenediaminetetraacetic acid
ELISA Enzyme-linked immunosorbent assay
FBS Foetal bovine serum
HEK293 Human embryonic kidney
HRP Horseradish peroxidase
hTERT Human telomerase reverse transcriptase
L-Dopa Levodopa
LRP/LR 37 kDa Laminin Receptor Precursor/67 kDa high affinity Laminin Receptor
MTT 3-(4,5-dimethylthiazol-2-yl)-2,5-diphenyltetrazolium bromide
NAC Non-amyloid-O component of plaques
PBS Phosphate-buffered saline
PCA Protocatechuic acid
PD Parkinson's disease
P/S Penicillin/Streptomycin
PVDF Polyvinylidene difluoride
RIPA Radioimmunoprecipitation assay
SDS PAGE Sodium dodecyl sulfate polyacrylamide gel electrophoresis SNPC Substantia nigra pars compacta
UPS Ubiquitin-proteasome system

Experimental Procedure (Example 1)

Cell Culture

The HEK293 cell line was used as it is commonly used in Parkinson's disease (PD) research (Schlachetzki et al., 2013). The cell culture media was made up from Dulbecco's Modified Eagle Medium (DMEM) (Hyclone) and Ham's F12 with a ratio of 1:1. The mixture was supplement with 1% penicillin/streptomycin (P/S) and 15% foetal bovine serum (FBS) to create a supplemented media that will provide the cells with essential nutrients that include growth factors and P/S to prevent contamination with bacteria and fungi. The nutrient media was renewed when it was required. The cells were cultured at in an incubator, that maintains the humidity, pH, at 37° C. and 5% $CO_2$ atmospheric composition to mimic in vivo conditions. Once the cells reached a confluency of 80%, they were passaged by washing with phosphate-buffered saline (PBS) followed by resuspension by the addition of trypsin-EDTA. Once the cells were re-suspended media was added to inactivate the trypsin and the cell suspension was diluted into a new flask. Fresh media was added to both flasks. Both transfected and non-transfected cells were harvested for further applications. The SH-SY5Y cell line is another cell line that is widely used for PD research as it displays a catecholaminergic phenotype. SH-SY5Y cells were also received after transfection was confirmed. The cells were maintained in the same conditions as the HEK293 cells. The SH-SY5Y cells were used for the MTT cell viability assay. LRP::FLAG overexpressing HEK293 cells in the presence of 1-Methyl-4-phenylpyridinium iodide (MPP+), a PD inducer, was also investigated. Late stage colorectal carcinoma cells (DLD-1) cells were used for certain confocal microscopy studies with parkin protein.

Cell Transfections

Transfection of cells is used to overexpress a protein of interest. Non-transfected HEK293 cells will be used as a control. In this study transfection was used to stably overexpress LRP::FLAG by using the DNA construct, pCIneo-moLRP::FLAG (Vana & Weiss, 2006). By overexpression LRP::FLAG, the effect on α-Synuclein could be determined. Transfection was performed in a T25 flask (25 $cm^2$) once HEK293 cells had reached 50-70% confluency, following the Clontech Xfect™ transfection protocol. Briefly, 10 μg pCIneo-moLRP::FLAG plasmid DNA was made up to a final volume of 200 μl Xfect Reaction Buffer, following this 3 μl Xfect Polymer was added. This solution was then incubated for 10-minutes at room temperature, to allow the formation of nanoparticle complexes to form. The nanoparticle complexes containing the plasmid DNA were then added to the subconfluent cell culture followed by resuspension and a 48-hour incubation at 37° C. and 5% $CO_2$ in a humidified incubator. All media was removed after incubation for 48-hours and replaced with fresh complete growth media.

Transfected cells were then treated with 800 ng/ml Geneticin, as a selective treatment and thereafter 400 ng/ml to maintain the transfected cell population.

Confocal Microscopy

Confocal microscopy is a visualisation tool that is used to determine the localisation of fluorescently labelled proteins of interest. Confocal microscopy was used in this study to determine whether LRP/LR colocalises with α-Synuclein. In a 6-well plate, cells were seeded onto a coverslip (Labocare—18×18 mm; 0.19 mm thick) at a density of $1.2\times10^5$ cells per well. The cells were then incubated overnight at 37° C. and 5% CO2 in a humidified incubator to allow cell attachment. The remainder of the experiment was performed with gentle shaking. Following incubation, the cells were washed for 3 minutes in 2 ml 1×PBS. The cells were then fixed onto a coverslip, with 2 ml 4% formaldehyde, for 20 minutes at room temperature. Once the cells were fixed the cells were washed 3 times as above followed by permeabilisation with 3 ml 0.1% Triton X-100 for 20 minutes at room temperature. The cells were washed as above followed by blocking with 2 ml 0.5% Bovine Serum Albumin (BSA) in 1×PBS for 25 minutes. Once the cells were blocked, one wash with 2 ml PBS for 2 minutes was performed. The primary antibody was diluted (1/200) in 500 μl 0.5% BSA and added to the cells followed by incubation at 4° C. overnight. Following the incubation, the cells were washed 3 times with 2 ml 0.5% BSA in 1×PBS for 2 minutes. The secondary antibody was then diluted (1/500) in 500 μl 0.5% BSA and added to the cells followed by incubation for one hour at room temperature in the dark. The cells were then washed 3 times with 2 ml 1×PBS for 2 minutes in the dark. In order to stain the nucleus, 1 ml of 0.1 μg/ml diamidino-2-phenylindole (DAPI) was added to the cells. The coverslips were then incubated for 5 minutes in the dark at room temperature. followed by 4 washes with 2 ml 1×PBS for 2 minutes each, in the dark. The coverslips were then mounted on a glass microscope slide with Sigma Fluoromount (Sigma) and incubated for one and a half hours in the dark. The samples were then stored at 4° C. until it was needed for visualisation with the Zeiss LSM 780 confocal microscope. For a list of all antibodies used, see Table 1.

TABLE 1

| List of antibodies used in confocal microscopy | |
|---|---|
| **Detection of LRP/LR** | |
| Primary Antibody | Human IgG1-iS18 |
| Secondary Antibody | Anti-human FITC |
| **Detection of α-synuclein** | |
| Primary Antibody | Rabbit Anti-α-synuclein |
| Secondary Antibody | Anti-rabbit APC |
| **Detection of LRP::FLAG** | |
| Primary antibody | Anti-FLAG Cy3 |

Protein Extraction from Cells:

Protein samples were extracted from cell lysates in order to determine the protein concentration and to perform western blot analysis. In order to extract protein samples from the cells, cell lysates were prepared. Cells were first harvested by removing all media from the flasks and washed with 5 ml 1×PBS. Cells were then resuspended in the culture flasks by adding 2 ml Trypsin/EDTA and incubated for 5 minutes at 37° C. In order to inactivate the Trypsin/EDTA 8 ml culture media was added to the flasks and the resuspended cells were transferred to 15 ml Falcon centrifuge tubes and centrifuged for 10 minutes at 5000 rpm. The supernatant was then discarded, followed by the addition of 100-250 μl 1× Radioimmunoprecipitation assay (RIPA) buffer to the remaining cell pellet. The RIPA buffer was made up with of 1% Triton X-100, 150 mM NaCl, 0.1% Sodium dodecyl sulfate (SDS), 0.5% sodium deoxycholate, 50 mM Tris-HCl (pH 8.0) and 5 mM ethylenediaminetetraacetic acid (EDTA) (pH 8.0) The amount of RIPA buffer added was dependent on the size of the cell pellet. The pelleted cells were then resuspended in the RIPA buffer followed by incubation for 15 minutes at 4° C. In order to determine the protein concentration of the prepared cell lysates, a BCA assay was performed prior to western blot analysis.

BCA Assay

The total protein concentration from the cell lysates was determined by performing the Bicinchoninic assay (BCA). This assay determines the protein concentration by focusing on $Cu^{2+}$ ions. $Cu^{+}$ is formed when the $Cu^{2+}$ is reduced by the peptide bond in proteins. The $Cu^{+}$ ions then form a complex with the BCA which results in a purple product that can be measured by absorbance. Briefly, BSA protein standards were prepared with a final concentration of 0, 0.2, 0.4, 0.6, 0.8 and 1 mg/ml. 10 μl of each standard was added to a well in a 96-well plate in triplicate. Protein samples with unknown concentration were then added at 3 μl per well, in triplicate. Distilled water was then added to the protein samples to make up a final volume of 10 μl. BCA and $CuSO_4$ were added to each well in a 29/30 and 1/30 ratio of BCA and $CuSO_4$, respectively. The samples were then incubated for 30 minutes at 37° C. An enzyme-linked immunosorbent assay (ELISA) plate reader was used to read the absorbance at 562 nm. A BCA protein standard curve was constructed using the optical densities of the BSA protein standards. The standard curve was then used to extrapolate the protein concentrations. Samples were then standardised to 2 mg/ml for western blot analysis.

SDS PAGE

Sodium dodecyl sulfate polyacrylamide gel electrophoresis (SDS PAGE) analysis was performed to separate the prepared proteins samples according to the proteins molecular weight prior to western blotting. SDS binds to the proteins causing the proteins to denature and gain a net negative charge. The overall net charge will be proportional to the molecular weight of the proteins. Electrophoresis of the proteins will cause the proteins to migrate from the negative terminal to the positive terminal. The migration allows the proteins to pass through pores according to their molecular weight. Once the extracted protein was quantified the protein sample was added to Blue Loading Buffer that contained 40 mM of dithiothreitol in order to obtain a final protein concentration of 25 μg for α-Synuclein and LRP::FLAG and 10 μg for LRP detection. In order to detect α-Synuclein and LRP::FLAG, a 15% (w/v) polyacrylamide gel was used and a 12% (w/v) polyacrylamide gel was used to detect LRP. A PiNK Plus Prestained Protein Ladder (GeneDireX) was loaded along with the protein samples onto each gel.

The proteins were then separated for 45 minutes at 150 V per gel. Western blot analysis was then performed.

Western Blotting

To determine the relative levels of LRP::FLAG, LRP and α-Synuclein western blotting was performed. Western blotting is used for the immunological detection of proteins by using labelled antibodies.

Firstly, protein extraction was performed, followed by separation of the proteins on an SDS PAGE gel by electrophoresis. Once the proteins were separated filter papers were soaked in 1× transfer buffer and a polyvinylidene difluoride (PVDF) membrane was cut to size and activated in methanol. Transfer buffer was made up of 192 mM glycine, 20% (w/v) methanol 25 and mM Tris base. A semi-dry electrophoretic transfer apparatus was used. Three filter papers were placed on the transfer apparatus followed by the PVDF membranes. The polyacrylamide gels were then placed on top of the PDVF membranes followed by three more filter papers. The transfer apparatus was closed after being filled up to the required amount with 1× transfer buffer. The proteins were transferred for 50 minutes at 300 mA. The membrane was then blocked using 3% BSA in PBS-TWEEN for 1 hour followed by five, five-minute washes in 0.1% PBS-TWEEN. Membranes were fixed with 0.4% formaldehyde prior to blocking in order to detect α-Synuclein due to its small molecular weight. The primary antibody was diluted in 3% BSA in PBS-TWEEN, added to the blots and incubated overnight at 4° C. Another five, five-minute washes were performed, and the secondary antibody was diluted in 3% BSA and then added followed by incubation for 1 hour at room temperature. Five washes were then performed followed by visualisation with Clarity™ Western ECL Blotting Substrate (Bio-Rad) and the ChemiDoc™ Imaging System (Bio-Rad). The Image Lab 5.1 software(Bio-Rad) was used to perform densitometric analysis and all values were normalised against the loading control β-actin.

TABLE 2

Antibodies that was used for the detection of LRP::FLAG, α-Synuclein and LRP/LR in western blotting

| | |
|---|---|
| **Detection of LRP::FLAG** | |
| Primary Antibody | Rabbit anti-FLAG |
| Secondary Antibody | Anti-rabbit HRP |
| **Detection of LRP** | |
| Primary Antibody | Human anti-LRP/LR IgG-iS18 |
| Secondary Antibody | Anti-human HRP |
| **Detection of α-synuclein** | |
| Primary Antibody | Rabbit Anti-α-synuclein |
| Secondary Antibody | Anti-rabbit HRP |
| **β-actin** | |
| Primary Antibody | Murine anti-β-actin-peroxidase. |

MTT Assay

The effects of treatment of cells with a specific substance or protein on cell viability can be determined by the MTT (3-(4,5-dimethylthiazol-2-yl)-2,5-diphenyltetrazolium bromide) assay (Riss et al., 2016). MTT is a tetrazolium salt that is yellow in colour that is converted to the purple formazan crystals by the mitochondrial enzyme succinate dehydrogenase (Stockert et al., 2012). The succinate dehydrogenase is only active in viable cells and therefore only viable cells will convert MTT to formazan (Stockert et al., 2012). The MTT assay was chosen over other cell viability assays, such as the ATP assay, the resoazurin reduction assay and the protease viability marker assay, due to its high throughput screening. For this study, HEK293 cells were first seeded at $1.4\times10^4$ cells per well in a 24-well plate while SH-SY5Y cells were seeded at $1.8\times10^4$ due to a slower growth rate. The cells were then incubated overnight to allow reattachment. Cells were then treated with 200 nM and 500 nM α-Synuclein, in order to induce a PD-like state. Following treatment, the cells were incubated for 48 hours to determine the effects of α-Synuclein on cell viability and incubated for 48 hours. The known apoptosis inducer, protocatechuic acid (PCA) was used as the positive control. Following incubation, 200 μl of 1 mg/ml MTT was then added to each well and incubated for 2 hours at 37° C. to allow the formation of formazan crystals. The remaining MTT was discarded and the formazan crystals were dissolved by the addition of 200 μl dimethyl sulfoxide (DMSO). The samples were then added to a 96-well plate at 100 μl in duplicates and the absorbance was read at 570 nm using an ELISA plate reader. High absorbance is indicative of a high number of viable cells.

Statistical Evaluation

Statistical evaluation of the data was conducted by performing the student's t-test with a confidence interval of 95% and as a result, results were considered significant when the p-value was lower than 0.05 was considered significant (*$p<0.05$, $p<0.01$ and *$p<0.001$) (Johnston, 1970).

Results (Example 1)

Overexpression of LRP::FLAG in HEK293 Cells

Figure 2A:
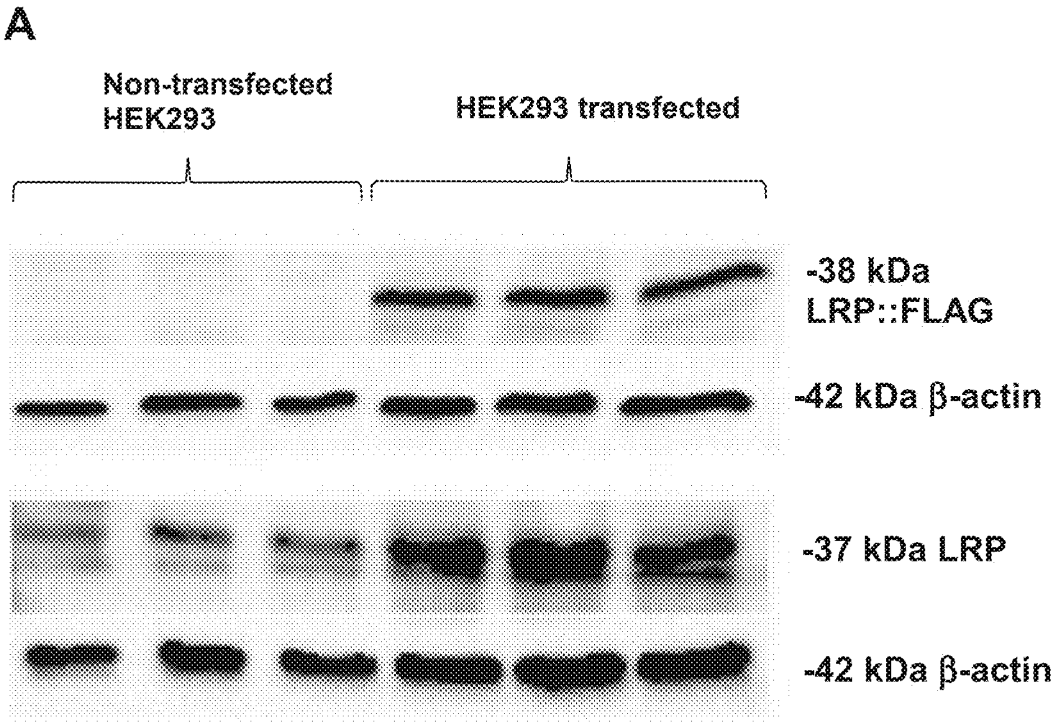
FIGS. 2A and B show Western blot and densitometric analysis of protein lysates of HEK293 cells Western blot analysis was performed on pCIneo-LRP::FLAG transfected HEK293 and non-transfected HEK293 cells. Primary antibody used were raised against LRP and FLAG. Secondary antibodies were coupled with HRP. A HRP coupled primary antibody was used to detect β-actin. pCIneo-LRP::FLAG transfections resulted in LRP::FLAG overexpression and increase of total LRP levels.

The role LRP/LR plays in PD has not yet been determined. To determine the role that LRP/LR plays in PD, HEK293 cells were stably transfected to overexpress LRP::FLAG. The pCIneo-moLRP::FLAG plasmid was used to achieve this. Once cells were transfected, western blot analysis was performed to confirm that the transfection was successful (FIG. 6A). In addition, total LRP protein levels were examined in both transfected and non-transfected HEK293 cell lines and a loading control, β-actin was used (FIG. 2A).

Figure 2B:
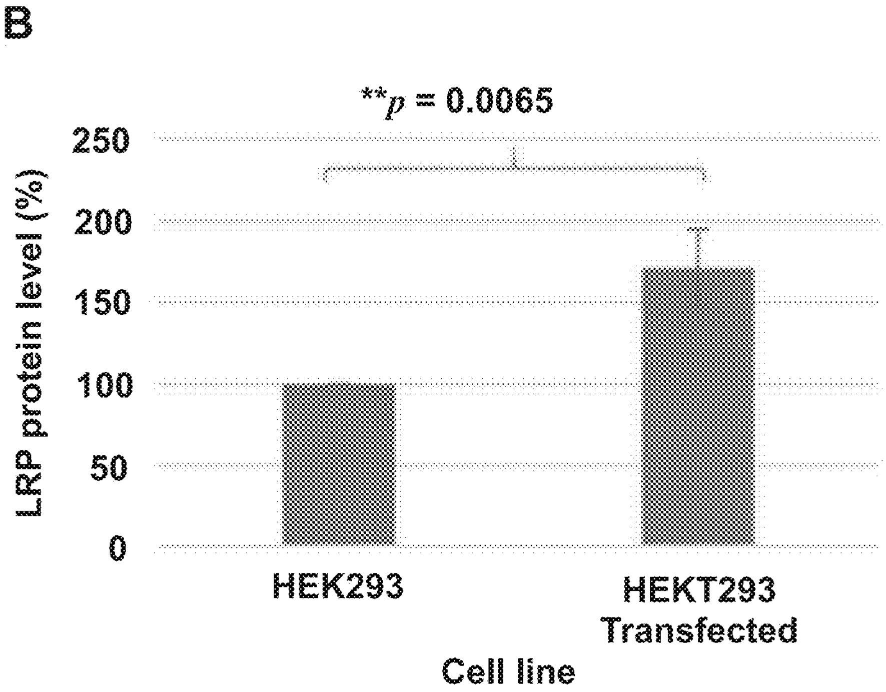

Western blot analysis was performed to detect LRP::FLAG and to determine total LRP protein levels in the transfected and non-transfected HEK293 cells. LRP::FLAG was exclusively detected in transfected HEK293 cells (FIG. 2A: lanes 4-6). Therefore, transfection was successful and HEK293 transfected cells were overexpressing LRP::FLAG. When comparing LRP protein levels of non-transfected (FIG. 2A: lanes 1-3) and transfected (FIG. 2A: lanes 4-6) HEK293 cells, an increase in LRP/LR protein levels is seen. Densitometric and statistical analysis revealed a significant increase in total LRP levels and show that overexpression of LRP::FLAG increased LRP levels by 71.24% (FIG. 2B.). The loading control, β-actin, was used.

Overexpression of LRP::FLAG in HEK293 Cells Increases α-Synuclein Levels and LRP/LR Co-Localizes with α-Synuclein in HEK293 Cells In order to determine whether α-Synuclein and LRP/LR co-localise, confocal microscopy was performed. Transfected HEK293 and non-transfected cells were viewed under the confocal microscope at a magnification of 630λ. The relative protein levels were also examined and compared in transfected and non-transfected HEK293 cells. Co-localization of α-Synuclein and LRP/LR occurred in the cytoplasm as well as the cell surface of both non-transfected and transfected HEK293 cells. Additionally, it was found that LRP::FLAG transfected HEK293 cells express more α-Synuclein as shown by the increase in the intensity of the fluorescence in FIG. 3H compared to FIG. 3A. The co-localisation images confirm co-localisation between α-Synuclein and LRP/LR and reveal that cells overexpressing LRP::FLAG have a greater degree of co-localization. The diagonals seen in the 2D cytofluorogram in FIG. 3G and FIG. 3N also confirms colocalization between α-Synuclein and LRP/LR.

The 10 kDa CTD of α-Synuclein Increases in LRP::FLAG Overexpressing Cells

Figure 4B:
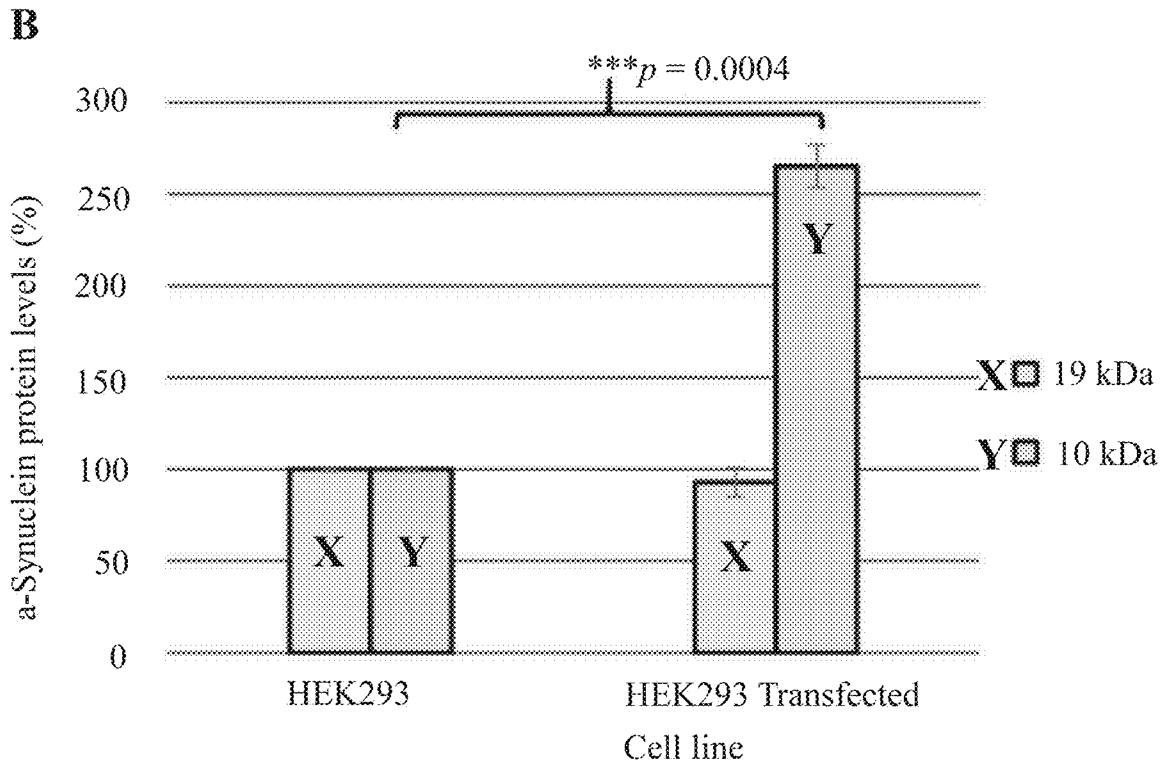

To determine the effect that overexpressing LRP::FLAG has on α-Synuclein protein levels, western blot analysis was performed on both transfected and non-transfected HEK293 cell lines (FIG. 4). When comparing α-Synuclein protein levels in non-transfected (FIG. 4A: lanes 1-3) and transfected (FIG. 4A: lanes 4-6) HEK293 cells, no difference was observed in the 19 kDa full-length α-Synuclein protein levels. However, an increase was seen in the 10 kDa CTD of α-Synuclein. Densitometric analysis of the western blot confirm this and showed that the CTD of α-Synuclein protein levels increased by 165.22% (FIG. 4B.).

Overexpression of LRP::FLAG Increases Cell Viability in HEK293 Cells and SH-SY5Y Cells Treated with 200 nM and 500 nM α-Synuclein To determine the effect that overexpressing LRP::FLAG has on cell viability in α-Synuclein treated cells an MTT assay was performed. MTT assay was performed on both HEK293 and SH-SY5Y transfected and non-transfected cell lines. Cells were treated with 200 nM and 500 nM α-Synuclein in order to induce a PD-like state. MTT analysis showed a significant decrease in cell viability in both HEK293 and SH-SY5Y transfected and non-transfected cell lines when cells were treated with the positive control, PCA, a known apoptotic inducer (FIGS. 5 and 6.), as expected. When cells we treated with 200 nM and 500 nM α-Synuclein cell viability decreased significantly in HEK293 non-transfected cells (FIG. 5). However, no significant increase or decrease was seen in the SH-SY5Y non-transfected cells treated with 200 nM and 500 nM α-Synuclein (FIG. 6.). A slight increase in cell viability was seen in both HEK293 and SH-SY5Y LRP::FLAG transfected cells treated with 200 nM and 500 nM α-Synuclein, however, this increase was not significant (FIGS. 5 and 6.). Due to time constraints, the SH-SY5Y cell line was only used in the MTT cell viability assay.

Overexpression of LRP::FLAG Increases Cell Viability in HEK293 Cells Treated with 500 uM and 750 nM 1-Methyl-4-Phenylpyridinium Iodide (MPP+)

MTT assay analysis of pCIneo-moLRP::FLAG transfected and non-transfected HEK293 cells indicating a significant increase in cell viability in LRP::FLAG overexpressing HEK293 cells in the presence of 500 uM and 750 nM 1-Methyl-4-phenylpyridinium iodide (MPP+) for 48 hours and 72 hours was only conducted (see FIGS. 7A and 7B).

Discussion (Example 1)

LRP::FLAG was overexpressed in the HEK293 in vitro PD model, in order to establish whether a relationship between LRP/LR and α-Synuclein exists and LRP/LR and parkin exits.

LRP/LR Co-Localises with α-Synuclein and Parkin

Once LRP::FLAG expression was confirmed in HEK293 cells by western blot analysis (FIG. 2), LRP levels were examined. Western blot analysis confirmed that overexpression of LRP::FLAG results in a 71.24% increase in total LRP protein level in comparison to non-transfected cells (FIG. 2). Thereafter, confocal microscopy was performed to determine whether LRP/LR and α-Synuclein colocalise.

Figure 3:
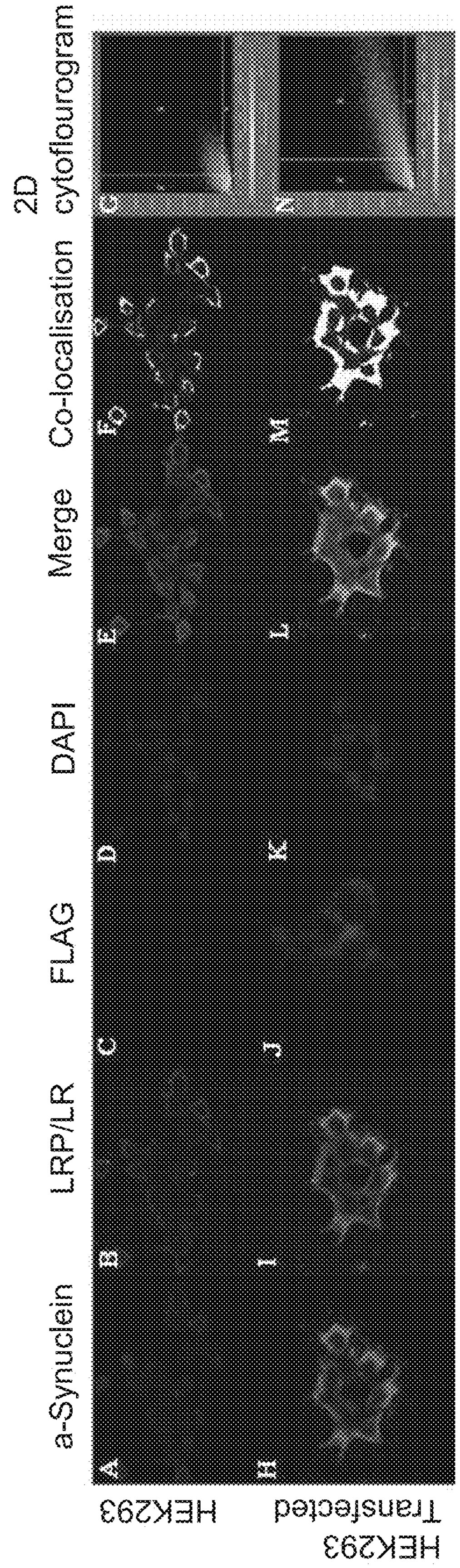

Confocal microscopy demonstrated that LRP/LR and α-Synuclein colocalise in the cytoplasm as well as on the cell surface in non-transfected HEK293 cells (FIG. 3). The colocalization was confirmed by the merged, colocalization and the diagonal in the 2D cytofluorogram images. A few studies have demonstrated that α-Synuclein is mainly found in the cytoplasm (Guardia-Laguarta et al., 2015). Other studies showed that α-Synuclein is able to bind to membranes once stimulated (Eliezer et al., 2001; Jao et al., 2004). It remains unclear what the exact stimulus is. This provides evidence that there is an interaction between LRP/LR and α-Synuclein as they have they localise in the same subcellular compartments. Without being limited to theory, LRP/LR could act as a stimulus that results in the membrane binding.

Confocal microscopy not only revealed the colocalization between LRP/LR and α-Synuclein but it also revealed that following LRP::FLAG transfection, both LRP/LR and α-Synuclein protein levels increased (FIG. 4). Co-localisation, in LRP::FLAG overexpressing HEK293 cells, between LRP/LR and α-Synuclein was more pronounced when compared to non-transfected HEK293 cells due to the increase in protein levels of both α-Synuclein and LRP/LR. The increase in α-Synuclein levels observed in LRP::FLAG transfected HEK293 cells is further evidence that there is a possible interaction between LRP/LR and α-Synuclein.

In FIG. 3 primary antibodies used were raised against LRP and α-Synuclein. A Cy3 coupled primary antibody was used to detect FLAG. Secondary antibodies were coupled with FITC and Alexaflour 647. Panels A and H represent α-Synuclein in red and panels B and I represent LRP/LR in green.

LRP::FLAG is represented in panel C and J. Panels E and L, represent a merge of the α-Synuclein and LRP/LR. The yellow fluorescence indicates an overlap and possible interaction between α-Synuclein and LRP/LR. Panel A and B: LRP and α-Synuclein is expressed mainly on the cell surface where co-localisation occurs. Panel H and I: Upon pCIneo-LRP::FLAG transfection, LRP/LR and α-Synuclein levels increase. LRP/LR colocalizes in HEK293 cells (panel E-F) and this effect which is more pronounced in LRP::FLAG overexpressing cells (L-N). Colocalization occurs on the cell surface and intracellularly as indicated by the diagonal in the 2D cytofluorogram graphs (G and N).

FIG. 8 shows confocal microscopy at 630× magnification indicating expression levels and localization of LRP and parkin. Primary antibodies used were raised against LRP, parkin and hTERT.

Secondary antibodies were coupled with FITC, Cy3 and Alexaflour 647. Panels A to F represent DLD-1 cells while panels G to L represent DLD-1 cells that have been transfected with the pCIneo-LRP::FLAG plasmid. Panel A and G represent parkin in yellow and panel B and H represent LRP/LR in green. Panel D and I represent a merge of parkin and LRP/LR. Panel E and K represents the colocalization of the two proteins, where the white indicates an overlap and possible interaction between parkin and LRP/LR. Colocalization occurs intracellularly as indicated by the diagonal in the 2D cytofluorogram graphs (F) with 59/a of parkin colocalizing with 54% of LRP/LR in DLD-1 cells while in DLD-1 cells overexpressing LRP::FLAG 99% of parkin colocalizes with 22% of LRP. This supports overexpression of LRP/LR increases parkin protein levels in cells.

LRP::FLAG Overexpression Increases CTD of α-Synuclein and Increases Parkin Protein Western blot analysis also served to confirm the increase in α-Synuclein seen in confocal microscopy. However, no increase in the full length 19 kDa α-Synuclein protein levels was seen following LRP::FLAG transfection (FIG. 5.). Interestingly, a 165.22% increase in a second band below the full-length 19 kDa α-Synuclein was seen in the LRP::FLAG transfected HEK293 cells. Previous studies have showed that the CTD of α-Synuclein is 10 kDa and migrates below the full length 19 kDa α-Synuclein (Xu et al, 2015). The CTD plays an important role in preventing α-Synuclein aggregation by interacting with the NAC domain (Emamzadeh, 2016). Most studies focus on the NTD of α-Synuclein due to the many mutations that have been found in this domain and thus not many studies have been done on the CTD (Xu & Pu 2016). A recent study has demonstrated that truncation of the CTD alters the mechanism of α-Synuclein aggregation as well as the properties of the fibrils that are formed (van der Wateren et al., 2018). The same study also demonstrated that truncation of the CTD promotes α-Synuclein aggregation (van der Wateren et al., 2018). This suggests that the results seen from the western blots in this study are evidence that LRP/LR increases the CTD of α-Synuclein, which prevents the aggregation of α-Synuclein.

LRP::FLAG Overexpression Increases Cell Viability

To determine whether the increase in the CTD of α-Synuclein was positive or negative an MTT cell viability assay was performed. The MTT assay was performed on HEK293 non-transfected and transfected as well as SH-SY5Y non-transfected and transfected cell lines. The SH-SY5Y cell line is widely used in PD research as it produces both dopamine and noradrenaline thus displaying a catecholaminergic phenotype (Xicoy et al., 2017). Treatment of both LRP::FLAG overexpressing and non-transfected HEK293 cells with 200 nM and 500 nM α-Synuclein, resulted in a slight decrease in cell viability however no decrease was seen in the LRP::FLAG overexpressing and non-transfected SH-SY5Y cells. Interestingly, when comparing the cell viability of cells overexpressing LRP::FLAG with non-transfected cells a slight increase in cell viability was observed in both HEK293 and SH-SY5Y cell lines. No negative effects are observed in cell viability when overexpressing LRP::FLAG. These results could, however, be indicating that the increase in the CTD of α-Synuclein following LRP::FLAG transfection and thus overexpression of LRP::FLAG could rescue the cell from the effects of α-Synuclein treatment. The CTD is vital in maintaining the structure of the full-length α-Synuclein and prevents a conformation change that is important in the fibrillation process (Hong et al., 2011). The mechanism behind this protection would need to be investigated.

MTT assay analysis of pCIneo-moLRP::FLAG transfected and non-transfected HEK293 cells indicating a significant increase in cell viability in LRP::FLAG overexpressing HEK293 cells in the presence of 500 uM and 750 nM 1-Methyl-4-phenylpyridinium iodide (MPP+) for 48 hours (shown in FIG. 7A) and 72 hours (shown in FIG. 7B).

Conclusions (Example 1)

In conclusion, LRP/LR increases the C-terminal of α-Synuclein therein preventing is accumulation and/or aggregation and in so doing provides an effective compound to treat Parkinson's disease (PD). The Applicant demonstrates that LRP/LR not only co-localises with α-Synuclein but overexpression of LRP::FLAG increases levels of the CTD. Any observed increase in the CTD plays a protective role in cells treated with α-Synuclein. LRP/LR is also shown to colocalize with parkin. Therefore, therapeutic approaches aiming to increase LRP/LR protein levels might result in a potential therapeutic treatment for PD.

References (Example 1)

Ahmed, S., Passos, J. F., Birket, M. J., Beckmann, T., Brings, S., Peters, H., Birch-Machin, M. A., von Zglinicki, T. and Saretzki, G., 2008. Telomerase does not counteract telomere shortening but protects mitochondrial function under oxidative stress. Journal of cell science, 121(7), pp.1046-1053.

Ardini, E., Pesole, G., Tagliabue, E., Magnifico, A., Castronovo, V., Sobel, M. E., Colnaghi, M. I. and Mdnard, S., 1998. The 67-kDa laminin receptor originated from a ribosomal protein that acquired a dual function during evolution. Molecular biology and evolution, 15(8), pp.1017-1025.

Auluck, P. K., Caraveo, G. and Lindquist, S., 2010. α-Synuclein: membrane interactions and toxicity in Parkinson's disease. Annual review of cell and developmental biology, 26, pp.211-233.

Bendor, J. T., Logan, T. P. and Edwards, R. H., 2013. The function of α-Synuclein. Neuron, 79(6), pp. 1044-1066.

Chai, C. and Lim, K. L., 2013. Genetic insights into sporadic Parkinson's disease pathogenesis. Current genomics, 14(8), pp. 486-501.

Chauhan, A. and Jeans, A. F., 2015. Is Parkinson's disease truly a prion-like disorder? An appraisal of current evidence. Neurology research international, 2015.

Chen, M. S., Fornace Jr, A. and Laszlo, A., 1996. Characterization of an hsp70 related clone encoding a 33 kDa protein with homology to a protein which associates with polysomes. Biochimica et Biophysica Acta (BBA)-Protein Structure and Molecular Enzymology, 1297(2), pp.124-126.

Chetty, C. J., Ferreira, E., Jovanovic, K. and Weiss, S. F., 2017. Knockdown of LRP/LR induces apoptosis in pancreatic cancer and neuroblastoma cells through activation of caspases. Experimental cell research, 360(2), pp.264-272.

Dauer, W. and Przedborski, S., 2003. Parkinson's disease: mechanisms and models. Neuron, 39(6), pp. 889-909.

Dexter, D. T. and Jenner, P., 2013. Parkinson disease: from pathology to molecular disease mechanisms. Free Radical Biology and Medicine, 62, pp.132-144.

Dias, B. D. C., Jovanovic, K., Gonsalves, D., Moodley, K., Reusch, U., Knackmuss, S., Penny, C., Weinberg, M. S., Little, M. and Weiss, S. F., 2013. Anti-LRP/LR specific antibody IgG1-iS18 and knock-down of LRP/LR by shRNAs rescue cells from Aβ 42 induced cytotoxicity. Scientific reports, 3, p.2702.

Dias, B. D. C., Jovanovic, K., Gonsalves, D., Moodley, K., Reusch, U., Knackmuss, S., Weinberg, M. S., Little, M. and Weiss, S. F., 2014. The 37 kDa/67 kDa laminin receptor acts as a receptor for Aβ 42 internalization. Scientific reports, 4, p.5556.

Dickson, D. W., 2012. Parkinson's disease and parkinsonism: neuropathology. Cold Spring Harbor perspectives in medicine, p.a009258.

DiGiacomo, V. and Meruelo, D., 2016. Looking into laminin receptor: critical discussion regarding the non-integrin 37/67-kDa laminin receptor/RPSA protein. Biological Reviews, 91(2), pp.288-310.

Dolgacheva, L. P., Fedotova, E. I., Abramov, A. Y. and Berezhnov, A. V., 2018. Alpha-Synuclein and Mitochondrial Dysfunction in Parkinson's Disease. Biochemistry (Moscow), Supplement Series A: Membrane and Cell Biology, 12(1), pp. 10-19.

Eliezer, D., Kutluay, E., Bussell Jr, R. and Browne, G., 2001. Conformational properties of α-Synuclein in its free and lipid-associated statesl. Journal of molecular biology, 307(4), pp.1061-1073.

Emamzadeh, F. N., 2016. Alpha-Synuclein structure, functions, and interactions. Journal of research in medical sciences: the official journal of Isfahan University of Medical Sciences, 21.

Ferreira, E., Bignoux, M. J., Otgaar, T. C., Tagliatti, N., Jovanovic, K., Letsolo, B. T. and Weiss, S. F., 2018. LRP/LR specific antibody IgG1-iS18 impedes neurodegeneration in Alzheimer's disease mice. Oncotarget, 9(43), p.27059.

Ford C L, Randal-Whitis L, Ellis S R. Yeast proteins related to the p40/laminin receptor precursor are required for 20S ribosomal RNA processing and the maturation of 40S ribosomal subunits. Cancer Res 1999:59(3):704-10

Fu, H., Subramanian, R. R. and Masters, S. C., 2000. 14-3-3 proteins: structure, function, and regulation. Annual review of pharmacology and toxicology, 40(1), pp. 617-647.

Gauczynski, S., Nikles, D., El-Gogo, S., Papy-Garcia, D., Rey, C., Alban, S., Barritault, D., Lasmézas, C. I. and Weiss, S., 2006. The 37-kDa/67-kDa laminin receptor acts as a receptor for infectious prions and is inhibited by polysulfated glycanes. The Journal of infectious diseases, 194(5), pp.702-709.

Gauczynski, S., Nikles, D., El-Gogo, S., Papy-Garcia, D., Rey, C., Alban, S., Barritault, D., Lasmezas, C. I. and Weiss, S., 2006. The 37-kDa/67-kDa laminin receptor acts as a receptor for infectious prions and is inhibited by polysulfated glycanes. The Journal of infectious diseases, 194(5), pp.702-709.

Guardia-Laguarta, C., Area-Gomez, E., Schon, E. A. and Przedborski, S., 2015. Novel subcellular localization for α-Synuclein: possible functional consequences. Frontiers in neuroanatomy, 9, p.17.

Hong, D. P., Xiong, W., Chang, J. Y. and Jiang, C., 2011. The role of the C-terminus of human α-Synuclein: Intra-disulfide bonds between the C-terminus and other regions stabilize non-fibrillar monomeric isomers. FEBS letters, 585(3), pp.561-566.

Jao, C. C., Der-Sarkissian, A., Chen, J. and Langen, R., 2004. Structure of membrane-bound α-Synuclein studied by site-directed spin labeling. Proceedings of the National Academy of Sciences, 101(22), pp.8331-8336.

Jenner, P., 2003. Oxidative stress in Parkinson's disease. Annals of neurology, 53(S3).

Jones, DR., Moussaud, S. and McLean, P., 2014. Targeting heat shock proteins to modulate α-synuclein toxicity. Therapeutic advances in neurological disorders, 7(1), pp. 33-51.

Jovanovic, K., Gonsalves, D., Dias, B. D. C., Moodley, K., Reusch, U., Knackmuss, S., Penny, C., Weinberg, M. S., Little, M. and Weiss, S. F., 2013. Anti-LRP/LR specific antibodies and shRNAs impede amyloid beta shedding in Alzheimer's disease. Scientific reports, 3, p.2699.

Jovanovic, K., Chetty, C. J., Khumalo, T., Da Costa Dias, B., Ferreira, E., Malindisa, S. T., Caveney, R., Letsolo, B. T. and Weiss, S. F., 2015. Novel patented therapeutic approaches targeting the 37/67 kDa laminin receptor for treatment of cancer and Alzheimer's disease. Expert opinion on therapeutic patents, 25(5), pp.567-582.

Khumalo, T., Ferreira, E., Jovanovic, K., Veale, R. B. and Weiss, S. F., 2015. Knockdown of LRP/LR induces apoptosis in breast and oesophageal cancer cells. PloS one, 10(10), p.e0139584.

Khusal, R., Dias, B. D. C., Moodley, K., Penny, C., Reusch, U., Knackmuss, S., Little, M. and Weiss, S. F., 2013. In vitro inhibition of angiogenesis by antibodies directed against the 37 kDa/67 kDa laminin receptor. PloS one, 8(3), p.e58888.

Kinoshita K, Kaneda Y, Sato M, et al. LBP-p40 binds DNA tightly through associations with histones H2A, H2B, and H4. Biochem Biophys Res Commun 1998; 253(2):277-82.

Kitada, T., Asakawa, S., Hattori, N., Matsumine, H., Yamamura, Y., Minoshima, S., Yokochi, M., Mizuno, Y. and Shimizu, N., 1998. Mutations in the parkin gene cause autosomal recessive juvenile parkinsonism. Nature, 392(6676), p.605.

Klucken, J., Shin, Y., Masliah, E., Hyman, B. T. and McLean, P. J., 2004. Hsp70 reduces α-synuclein aggregation and toxicity. Journal of Biological Chemistry, 279(24), pp. 25497-25502. Lees, A., 2017. An essay on the shaking palsy. Brain, 140(3), pp. 843-848.

Leucht, C., Simoneau, S., Rey, C., Vana, K., Rieger, R., Lasmezas, C. I. and Weiss, S., 2003. The 37 kDa/67 kDa laminin receptor is required for PrPSc propagation in scrapie-infected neuronal cells. EMBO reports, 4(3), pp. 290-295.

Lima, M. M., Reksidler, A. B. and Vital, M. A., 2009. The neurobiology of the substantia nigra pars compacta: from motor to sleep regulation. In Birth, Life and Death of Dopaminergic Neurons in the Substantia Nigra (pp. 135-145). Springer, Vienna. Mandel, S. A., Morelli, M., Halperin, I. and Korczyn, A. D., 2010. Biomarkers for prediction and targeted prevention of Alzheimer's and Parkinson's diseases: evaluation of drug clinical efficacy. EPMA Journal, 1(2), pp.273-292.

Marinus, J., Zhu, K., Marras, C., Aarsland, D. and van Hilten, J. J., 2018. Risk factors for non-motor symptoms in Parkinson's disease. The Lancet Neurology.

Mbazima, V., Da Costa Dias, B., Omar, A., Jovanovic, K. and Weiss, S. F., 2010. Interactions between PrP (c) and other ligands with the 37-kDa/67-kDa laminin receptor. Front Biosci, 15(1150-1163), p.3667.

Muzerengi, S. and Clarke, C. E., 2015. Initial drug treatment in Parkinson's disease. Bmj, 351, p.h4669.

Oertel, W. and Schulz, J. B., 2016. Current and experimental treatments of Parkinson disease: A guide for neuroscientists. Journal of neurochemistry, 139, pp. 325-337.

Omar, A., Reusch, U., Knackmuss, S., Little, M. and Weiss, S. F., 2012. Anti-LRP/LR-specific antibody IgG1-iS18 significantly reduces adhesion and invasion of metastatic lung, cervix, colon and prostate cancer cells. Journal of molecular biology, 419(1-2), pp. 102-109.

Otgaar, T. C., Ferreira, E., Malindisa, S., Bernert, M., Letsolo, B. T. and Weiss, S. F., 2017. 37 kDa LRP::FLAG enhances telomerase activity and reduces senescent markers in vitro. Oncotarget, 8(49), p.86646.

Palacino, J. J., Sagi, D., Goldberg, M. S., Krauss, S., Motz, C., Wacker, M., Klose, J. and Shen, J., 2004. Mitochondrial dysfunction and oxidative damage in parkin-deficient mice. Journal of Biological Chemistry, 279(18), pp.18614-18622.

Rao, N. C., Barsky, S. H., Terranova, V. P. and Liotta, L. A., 1983. Isolation of a tumor cell laminin receptor. Biochemical and biophysical research communications, 111 (3), pp. 804-808.

Rieger, R., Edenhofer, F., Lasmezas, C. I. and Weiss, S., 1997. The human 37-kDa laminin receptor precursor interacts with the prion protein in eukaryotic cells. Nature medicine, 3(12), pp.1383-1388.

Riss, T. L., Moravec, R. A., Niles, A. L., Duellman, S., Benink, H. A., Worzella, T. J. and Minor, L., 2016. Cell viability assays.

Rocha, E. M., De Miranda, B. and Sanders, L. H., 2018. Alpha-Synuclein: pathology, mitochondrial dysfunction and neuroinflammation in Parkinson's disease. Neurobiology of disease, 109, pp.249-257.

Rodriguez-Araujo, G., Nakagami, H., Takami, Y., Katsuya, T., Akasaka, H., Saitoh, S., Shimamoto, K., Morishita, R., Rakugi, H. and Kaneda, Y., 2015. Low alpha-Synuclein levels in the blood are associated with insulin resistance. Scientific reports, 5, p.12081.

Savitt, J. M., Dawson, V. L. and Dawson, T. M., 2006. Diagnosis and treatment of Parkinson disease: molecules to medicine. The Journal of clinical investigation, 116(7), pp.1744-1754.

Schlachetzki, J., Saliba, S. W. and Oliveira, A. C. P. D., 2013. Studying neurodegenerative diseases in culture models. Revista brasileira de psiquiatria, 35, pp.S92-S100.

Seirafi, M., Kozlov, G. and Gehring, K., 2015. Parkin structure and function. The FEBS journal, 282(11), pp.2076-2088.

Shimura, H., Hattori, N., Kubo, S. I., Mizuno, Y., Asakawa, S., Minoshima, S., Shimizu, N., Iwai, K., Chiba, T., Tanaka, K. and Suzuki, T., 2000. Familial Parkinson disease gene product, parkin, is a ubiquitin-protein ligase. Nature genetics, 25(3), p.302.

Sidransky, E., Samaddar, T. and Tayebi, N., 2009. Mutations in GBA are associated with familial Parkinson disease susceptibility and age at onset. Neurology, 73(17), pp. 1424-1426.

Song, P., Trajkovic, K., Tsunemi, T. and Krainc, D., 2016. Parkin modulates endosomal organization and function of the endo-lysosomal pathway. Journal of Neuroscience, 36(8), pp.2425-2437.

Stefanis, L., 2012. α-Synuclein in Parkinson's disease. Cold Spring Harbor perspectives in medicine, 2(2), p.a009399.

Stockert, J. C., Blázquez-Castro, A., Cañete, M., Horobin, R. W. and Villanueva, A., 2012. MTT assay for cell viability: Intracellular localization of the formazan product is in lipid droplets. Acta histochemica, 114(8), pp.785-796.

Tarakad, A. and Jankovic, J., 2017, April. Diagnosis and management of Parkinson's disease. In Seminars in neurology (Vol. 37, No. 02, pp. 118-126). Thieme Medical Publishers.

Vamvaca K., Volles M. J. and Lansbury P. T. (2009) The first Nterminal amino acids of alpha-Synuclein are essential for alphahelical structure formation in vitro and membrane binding in yeast. J. Mol. Biol. 389, 413-424.

Vana, K. and Weiss, S., 2006. A trans-dominant negative 37 kDa/67 kDa laminin receptor mutant impairs PrPSc propagation in scrapie-infected neuronal cells. Journal of molecular biology, 358(1), pp. 57-66.

Van Der Wateren, I. M., Knowles, T., Buell, A., Dobson, C. M. and Galvagnion, C., 2018. C-terminal truncation of α-Synuclein promotes amyloid fibril amplification at physiological pH. Chemical Science.

Wakabayashi, K., Tanji, K., Mori, F. and Takahashi, H., 2007. The Lewy body in Parkinson's disease: Molecules implicated in the formation and degradation of α-synuclein aggregates. Neuropathology, 27(5), pp. 494-506.

Weiss, S. F., 2017. Bad Boy with a Twist: Targeting the 37 kDa/67 kDa Laminin Receptor for Treatment of Cancer and Neurodegenerative Diseases and for Changing Telomere Dynamics. Cell Cell. Life Sci. J., 2, p.000114.

Xicoy, H., Wieringa, B. and Martens, G. J., 2017. The SH-SY5Y cell line in Parkinson's disease research: a systematic review. Molecular neurodegeneration, 12(1), p.10.

Xu, B., Liu, W., Deng, Y., Yang, T. Y., Feng, S. and Xu, Z. F., 2015. Inhibition of calpain prevents manganese-induced cell injury and alpha-Synuclein oligomerization in organotypic brain slice cultures. PloS one, 10(3), p.e0119205.

Xu, L. and Pu, J., 2016. Alpha-Synuclein in Parkinson's disease: from pathogenetic dysfunction to potential clinical application. Parkinson's Disease, 2016.

Yang, Y., Nishimura, I., Imai, Y., Takahashi, R. and Lu, B., 2003. Parkin suppresses dopaminergic neuron-selective neurotoxicity induced by Pael-R in *Drosophila*. Neuron, 37(6), pp.911-924.

Yasuda, T. and Mochizuki, H., 2010. The regulatory role of α-Synuclein and parkin in neuronal cell apoptosis; possible implications for the pathogenesis of Parkinson's disease. Apoptosis, 15(11), pp.1312-1321.

The Applicant believes that the invention provides for at least new and inventive compounds, pharmaceutical compositions, and/or methods to treat and/or prevent Parkinson's disease (PD).

The Applicant was very surprised that providing LRP/LR to the human or animal body i.e. upregulating its expression increases the C-terminal domain (CTD) of α-synuclein. Since the prior art teaches downregulation of LRP/LR in the treatment of another neurodegenerative disease, namely Alzheimer's disease (AD), the Applicant did not expect that upregulation of LRP/LR (or providing same to the human or animal body) would have any positive impact on a neurodegenerative disease such as PD.

Providing LRP/LR as part of a treatment protocol for PD would significantly limit any chance of unwanted side effects as it is a naturally occurring protein/peptide. This would certainly ameliorate at least one of the problems known in the prior art. While the invention has been described in detail with respect to specific embodiments and/or examples thereof, it will be appreciated that those skilled in the art, upon attaining an understanding of the foregoing may readily conceive of alterations to, variations of and equivalents to these embodiments. Accordingly, the scope of the present invention should be assessed as that of the claims and any equivalents thereto, which claims are appended hereto.

The invention claimed is:

1. A method comprising increasing the C-terminal domain (CTD) of α-synuclein in cells of a human or animal subject who has Parkinson's disease by treating the subject to provide the subject with overexpressed cellular levels of a 37 kDa/67 kDa laminin receptor precursor/high affinity laminin receptor (LRP/LR) as compared with cells that were not transfected to produce LRP/LR, wherein the LRP/LR comprises the amino acid sequence as set forth in SEQ ID NO: 1 or SEQ ID NO: 2, and wherein the LRP/LR is administered to the subject by transfecting the cells of the subject to produce the LRP/LR.

2. A method for increasing the C-terminal domain (CTD) of α-synuclein in cells of a human or animal body, the method comprising the following step:

transfecting the cells in the human or animal body to produce and overexpress a 37 kDa/67 kDa laminin receptor precursor/high affinity laminin receptor (LRP/LR), thereby increasing cellular levels of LRP/LR as compared with cells that were not transfected to produce LRP/LR, such that said increased cellular levels of LRP/LR either:

a) increase expression of the CTD of α-synuclein in the cells of the human or animal body, b) increase viability of the cells, or c) both (a) and (b), wherein the increased cellular levels of LRP/LR comprise the amino acid sequence as set forth in SEQ ID NO: 1 or SEQ ID NO: 2.

3. The method according to claim 2, further comprising the step of providing to the cells of the human or animal body levo-dopa and/or dopamine and/or monoamine oxidase B inhibitors.

* * * * *

SEQUENCE LISTING

<160> NUMBER OF SEQ ID NOS: 5

<210> SEQ ID NO 1
<211> LENGTH: 295
<212> TYPE: PRT
<213> ORGANISM: Homo sapiens

<400> SEQUENCE: 1

```
Met Ser Gly Ala Leu Asp Val Leu Gln Met Lys Glu Glu Asp Val Leu
1               5                   10                  15

Lys Phe Leu Ala Ala Gly Thr His Leu Gly Gly Thr Asn Leu Asp Phe
            20                  25                  30

Gln Met Glu Gln Tyr Ile Tyr Lys Arg Lys Ser Asp Gly Ile Tyr Ile
        35                  40                  45

Ile Asn Leu Lys Arg Thr Trp Glu Lys Leu Leu Leu Ala Ala Arg Ala
    50                  55                  60

Ile Val Ala Ile Glu Asn Pro Ala Asp Val Ser Val Ile Ser Ser Arg
65                  70                  75                  80

Asn Thr Gly Gln Arg Ala Val Leu Lys Phe Ala Ala Ala Thr Gly Ala
                85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
    130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Glu Lys Ala Val Thr Lys
    210                 215                 220

Glu Glu Phe Gln Gly Glu Trp Thr Ala Pro Ala Pro Glu Phe Thr Ala
225                 230                 235                 240

Thr Gln Pro Glu Val Ala Asp Trp Ser Glu Gly Val Gln Val Pro Ser
                245                 250                 255

Val Pro Ile Gln Gln Phe Pro Thr Glu Asp Trp Ser Ala Gln Pro Ala
            260                 265                 270

Thr Glu Asp Trp Ser Ala Ala Pro Thr Ala Gln Ala Thr Glu Trp Val
        275                 280                 285

Gly Ala Thr Thr Asp Trp Ser
    290                 295
```

<210> SEQ ID NO 2
<211> LENGTH: 295
<212> TYPE: PRT
<213> ORGANISM: Mus musculus

<400> SEQUENCE: 2

```
Met Ser Gly Ala Leu Asp Val Leu Gln Met Lys Glu Glu Asp Val Leu
1               5                   10                  15

Lys Phe Leu Ala Ala Gly Thr His Leu Gly Gly Thr Asn Leu Asp Phe
```

```
            20                  25                  30

Gln Met Glu Gln Tyr Ile Tyr Lys Arg Lys Ser Asp Gly Ile Tyr Ile
        35                  40                  45

Ile Asn Leu Lys Arg Thr Trp Glu Lys Leu Leu Leu Ala Ala Arg Ala
    50                  55                  60

Ile Val Ala Ile Glu Asn Pro Ala Asp Val Ser Val Ile Ser Ser Arg
65                  70                  75                  80

Asn Thr Gly Gln Arg Ala Val Leu Lys Phe Ala Ala Ala Thr Gly Ala
                85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
    130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Glu Lys Ala Val Thr Lys
    210                 215                 220

Glu Glu Phe Gln Gly Glu Trp Thr Ala Pro Ala Pro Glu Phe Thr Ala
225                 230                 235                 240

Ala Gln Pro Glu Val Ala Asp Trp Ser Glu Gly Val Gln Val Pro Ser
                245                 250                 255

Val Pro Ile Gln Gln Phe Pro Thr Glu Asp Trp Ser Ala Gln Pro Ala
            260                 265                 270

Thr Glu Asp Trp Ser Ala Ala Pro Thr Ala Gln Ala Thr Glu Trp Val
        275                 280                 285

Gly Ala Thr Thr Glu Trp Ser
    290                 295


<210> SEQ ID NO 3
<211> LENGTH: 8
<212> TYPE: PRT
<213> ORGANISM: Escherichia coli

<400> SEQUENCE: 3

Asp Tyr Lys Asp Asp Asp Asp Lys
1               5


<210> SEQ ID NO 4
<211> LENGTH: 194
<212> TYPE: PRT
<213> ORGANISM: Homo sapiens

<400> SEQUENCE: 4

Arg Phe Thr Pro Gly Thr Phe Thr Asn Gln Ile Gln Ala Ala Phe Arg
1               5                   10                  15

Glu Pro Arg Leu Leu Val Val Thr Asp Pro Arg Ala Asp His Gln Pro
            20                  25                  30

Leu Thr Glu Ala Ser Tyr Val Asn Leu Pro Thr Ile Ala Leu Cys Asn
```

```
        35                  40                  45

Thr Asp Ser Pro Leu Arg Tyr Val Asp Ile Ala Ile Pro Cys Asn Asn
    50                  55                  60

Lys Gly Ala His Ser Val Gly Leu Met Trp Trp Met Leu Ala Arg Glu
65                  70                  75                  80

Val Leu Arg Met Arg Gly Thr Ile Ser Arg Glu His Pro Trp Glu Val
                85                  90                  95

Met Pro Asp Leu Tyr Phe Tyr Arg Asp Pro Glu Glu Ile Glu Lys Glu
            100                 105                 110

Glu Gln Ala Ala Ala Glu Lys Ala Val Thr Lys Glu Glu Phe Gln Gly
        115                 120                 125

Glu Trp Thr Ala Pro Ala Pro Glu Phe Thr Ala Thr Gln Pro Glu Val
    130                 135                 140

Ala Asp Trp Ser Glu Gly Val Gln Val Pro Ser Val Pro Ile Gln Gln
145                 150                 155                 160

Phe Pro Thr Glu Asp Trp Ser Ala Gln Pro Ala Thr Glu Asp Trp Ser
                165                 170                 175

Ala Ala Pro Thr Ala Gln Ala Thr Glu Trp Val Gly Ala Thr Thr Asp
            180                 185                 190

Trp Ser


<210> SEQ ID NO 5
<211> LENGTH: 194
<212> TYPE: PRT
<213> ORGANISM: Mus musculus

<400> SEQUENCE: 5

Arg Phe Thr Pro Gly Thr Phe Thr Asn Gln Ile Gln Ala Ala Phe Arg
1               5                   10                  15

Glu Pro Arg Leu Leu Val Val Thr Asp Pro Arg Ala Asp His Gln Pro
            20                  25                  30

Leu Thr Glu Ala Ser Tyr Val Asn Leu Pro Thr Ile Ala Leu Cys Asn
        35                  40                  45

Thr Asp Ser Pro Leu Arg Tyr Val Asp Ile Ala Ile Pro Cys Asn Asn
    50                  55                  60

Lys Gly Ala His Ser Val Gly Leu Met Trp Trp Met Leu Ala Arg Glu
65                  70                  75                  80

Val Leu Arg Met Arg Gly Thr Ile Ser Arg Glu His Pro Trp Glu Val
                85                  90                  95

Met Pro Asp Leu Tyr Phe Tyr Arg Asp Pro Glu Glu Ile Glu Lys Glu
            100                 105                 110

Glu Gln Ala Ala Ala Glu Lys Ala Val Thr Lys Glu Glu Phe Gln Gly
        115                 120                 125

Glu Trp Thr Ala Pro Ala Pro Glu Phe Thr Ala Ala Gln Pro Glu Val
    130                 135                 140

Ala Asp Trp Ser Glu Gly Val Gln Val Pro Ser Val Pro Ile Gln Gln
145                 150                 155                 160

Phe Pro Thr Glu Asp Trp Ser Ala Gln Pro Ala Thr Glu Asp Trp Ser
                165                 170                 175

Ala Ala Pro Thr Ala Gln Ala Thr Glu Trp Val Gly Ala Thr Thr Glu
            180                 185                 190

Trp Ser
```